United States Patent
Cramp et al.

[11] Patent Number: 6,028,032
[45] Date of Patent: Feb. 22, 2000

[54] 1,3-OXAZIN-4-ONE DERIVATIVES AS HERBICIDES

[75] Inventors: Michael Colin Cramp, Ongar, United Kingdom; Yoshihiro Usui; Keiichi Hayashizaki, both of Ibaraki-ken, Japan

[73] Assignee: Rhone-Poulenc Agriculture Ltd., Ongar, United Kingdom

[21] Appl. No.: 08/981,569

[22] PCT Filed: Jun. 18, 1996

[86] PCT No.: PCT/EP96/02616

§ 371 Date: Apr. 13, 1998

§ 102(e) Date: Apr. 13, 1998

[87] PCT Pub. No.: WO97/00865

PCT Pub. Date: Jan. 9, 1997

[30] Foreign Application Priority Data

Jun. 23, 1995 [GB] United Kingdom .................... 9512819

[51] Int. Cl.[7] .......................... A01N 43/86; C07D 265/06
[52] U.S. Cl. .......................... 504/223; 504/130; 544/96; 544/97
[58] Field of Search ........................ 544/96, 97; 504/223, 504/130

[56] References Cited

U.S. PATENT DOCUMENTS

| | | | |
|---|---|---|---|
| 5,436,224 | 7/1995 | Hamatani et al. | 504/223 |
| 5,696,054 | 12/1997 | Go et al. | 504/223 |

FOREIGN PATENT DOCUMENTS

| | | |
|---|---|---|
| 0605726 | 7/1994 | European Pat. Off. . |
| 0747352 | 12/1996 | European Pat. Off. . |
| 93/15064 | 8/1993 | WIPO . |
| 95/10510 | 4/1995 | WIPO . |
| 95/18113 | 7/1995 | WIPO . |

*Primary Examiner*—Richard L. Raymond
*Attorney, Agent, or Firm*—Burns, Doane, Swecker & Mathis, L.L.P.

[57] ABSTRACT

1,3-oxazin-4-ones of formula (I),

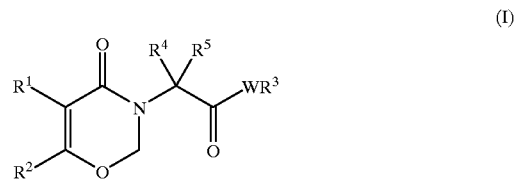

wherein $R^1$ represents phenyl optionally substituted; $R^2$ represents: a straight- or branched-chain alkyl having from one to ten carbon atoms which is substituted by one or more groups $R^8$ which may be the same or different; a straight- or branched-chain optionally halogenated alkenyl or alkynyl group having up to ten carbon atoms; or a group selected from cyano, —CHO, —COR$^7$, —CO$_2$H, —CO$_2$R$^7$, —COSR$^7$, —CONR$^9$R$^{10}$, —CH=NOH, —CH=NOR$^7$, —CH=NOCOR$^7$, —CH=NNR$^9$R$^{10}$, —CH$_2$CN, —CH$_2$NO$_2$ and oxiranyl; $R^3$ represents phenyl optionally substituted or $R^3$ represents a first five to seven membered heteroaromatic ring; said first ring being optionally fused and said first ring being linked to the nitrogen atom of the group NR$^6$ via one of the ring carbon atoms; $R^4$ and $R^5$ independently represent lower alkyl; W represents —NR$^6$—; $R^6$ represents hydrogen, lower alkyl, haloalkyl, alkenyl, alkynyl, —COR$^7$ or —CO$_2$R$^7$; and their use as herbicides.

19 Claims, No Drawings

1,3-OXAZIN-4-ONE DERIVATIVES AS HERBICIDES

This application is a 371 of PCT/EP 96/02616, filed Jun. 18, 1996.

BACKGROUND OF THE INVENTION

1. Field of the Invention

This invention relates to novel 1,3-oxazin-4-one derivatives, herbicidal compositions containing the same, and novel intermediates for preparing the same.

2. Description of the Related Art

Certain types of 1,3-oxazin-4-one derivatives, such as 2,3-dihydro-6-methyl-3-(1-methyl-1-phenylethyl)-5-phenyl-4H-1,3-oxazin-4-one, and their herbicidal activities are disclosed in for example International Patent Publication Nos. WO 93/15064 and WO 95/10510.

However, the compounds described in the above-mentioned publications differ from the compounds of the present invention since none of them have an acid amide substituent in the group attached to the nitrogen atom of the 3-position of a 1,3-oxazin ring.

SUMMARY OF THE INVENTION

According to the present invention, there is provided a 1,3-oxazin-4-one derivative of the formula (I):

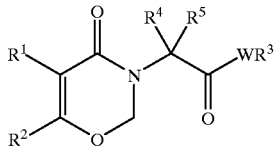

(I)

wherein:

$R^1$ represents phenyl optionally substituted by from one to five groups which may be the same or different selected from halogen, hydroxy, lower alkyl, haloalkyl, alkoxy, haloalkoxy, $-S(O)_nR^7$, $-CO_2R^7$, $-COR^7$, cyano, nitro, $-O(CH_2)_q-CO_2R^7$ and phenoxy;

$R^2$ represents:
 a straight- or branched-chain alkyl having from one to ten carbon atoms which is substituted by one or more groups $R^8$ which may be the same or different;
 a straight- or branched-chain optionally halogenated alkenyl or alkynyl group having up to ten carbon atoms;
 or a group selected from cyano, $-CHO$, $-COR^7$, $-CO_2H$, $-CO_2R^7$, $-COSR^7$, $-CONR^9R^{10}$, $-CH=NOH$, $-CH=NOR^7$, $-CH=NOCOR^7$, $-CH=NNR^9R^{10}$, $-CH_2CN$, $-CH_2NO_2$ and oxiranyl;

$R^3$ represents phenyl optionally substituted by from one to five groups which may be the same or different selected from halogen, hydroxy, lower alkyl, haloalkyl, alkoxy, haloalkoxy, $-S(O)_nR^7$, $-CO_2R^7$, $-COR^7$1 cyano, nitro, $-O(CH_2)_qCO_2R^7$ and phenoxy;

or $R^3$ represents a first five to seven membered heteroaromatic ring having from one to four ring heteroatoms which may be the same or different selected from nitrogen, oxygen and sulphur, said first ring being optionally fused to a phenyl ring or to a second five to seven membered heteroaromatic ring having from one to four heteroatoms which may be the same or different selected from nitrogen, oxygen and sulphur, to form a bicyclic ring system in which either ring is optionally substituted by from one to four groups which may be the same or different selected from halogen, hydroxy, lower alkyl, haloalkyl, alkoxy, haloalkoxy, $-S(O)_nR^7$, $-CO_2R^7$, $-COR^7$, cyano, nitro, $-O(CH_2)_qCO_2R^7$ and phenoxy, said first ring being linked to the nitrogen atom of the group $NR^6$ via one of the ring carbon atoms;

$R^4$ and $R^5$ independently represent lower alkyl;

W represents $-NR^6-$;

$R^6$ represents hydrogen, lower alkyl, haloalkyl, alkenyl, alkynyl, $-COR^7$ or $-CO_2R^7$;

$R^7$ represents lower alkyl or haloalkyl;

n represents zero, one or two;

q represents one or two;

$R^8$ represents a member of the group consisting of halogen, $-OH$, $-OR^7$, $-OCOR^7$, $-S(O)_nR^7$ and $-NR^9R^{10}$;

$R^9$ and $R^{10}$ independently represent hydrogen, lower alkyl or haloalkyl;

or an agriculturally acceptable salt thereof, which possesses valuable properties.

By the term "agriculturally acceptable salts" is meant salts the cations or anions of which are known and accepted in the art for the formation of salts for agricultural or horticultural use. Preferably the salts are water-soluble. Suitable salts with bases include alkali metal (eg. sodium and potassium), alkaline earth metal (eg. calcium and magnesium), ammonium and amine (eg. diethanolamine, triethanolamine, octylamine, morpholine and dioctylmethylamine) salts. Suitable acid addition salts, e.g. formed by compounds of formula (I) containing an amino group, include salts with inorganic acids, for example hydrochlorides, sulphates, phosphates and nitrates and salts with organic acids for example acetic acid.

In certain cases the groups $R^1$, $R^2$, $R^4$, $R^5$, $R^6$, $R^7$, $R^9$ and $R^{10}$ may give rise to stereoisomers and geometric isomers. All such forms are embraced by the present invention.

In the description the following terms are generally defined thus:

'lower alkyl' means a straight- or branched-chain alkyl group having one to six carbon atoms.

'haloalkyl' means a straight- or branched-chain alkyl group having one to six carbon atoms, substituted by one or more halogens.

'alkoxy' means a straight- or branched-chain alkoxy group having one to six carbon atoms.

'haloalkoxy' means a straight- or branched-chain alkoxy group having one to six carbon atoms, substituted by one or more halogens.

'halogen' means a fluorine, chlorine, bromine or iodine atom.

In the description that follows a number of preferred classes (because of their herbicidal properties) of compounds of formula (I) above are disclosed.

Compounds of formula (I) above in which $R^1$ represents phenyl optionally substituted by one or more groups selected from halogen, lower alkyl and haloalkyl are preferred. More preferably $R^1$ represents phenyl.

A further preferred class of compounds of formula (I) above are those wherein $R^2$ represents a straight- or branched-chain alkyl having from one to four carbon atoms substituted by one to three groups $R^8$ which may be the same or different. More preferably $R^2$ represents methyl substituted by one to three groups $R^8$ which may be the same or different.

$R^8$ preferably represents $-S(O)_nR^7$, (wherein $R^7$ is alkyl, most preferably methyl) or halogen.

Compounds in which $R^2$ represents methyl substituted by fluorine, methoxy, ethoxy and $-S(O)_nCH_3$ are preferred.

Compounds of formula (I) above in which $R^6$ is hydrogen are especially preferred.

Compounds of formula (I) above in which $R^3$ represents phenyl optionally substituted by one or two groups which be the same or different selected from halogen (e.g. fluorine) and haloalkyl (e.g. trifluoromethyl) are also preferred.

Compounds of formula (I) above in which $R^4$ and $R^5$ each represent methyl are especially preferred.

A particularly preferred class of compounds of formula (I) are those wherein:

$R^1$ represents phenyl optionally substituted by one or more groups which may be the same or different selected from halogen, methoxy and optionally halogenated methyl;

$R^2$ represents methyl substituted by a fluorine atom, $-S(O)_nR$, $-OCH_3$ or $-OCH_2CH_3$;

$R^3$ represents a phenyl ring substituted by one to three groups which may be the same or different selected from halogen, optionally halogenated methyl and $NO_2$;

$R^4$ and $R^5$ represent methyl;

W represents $-NH-$;

$R^7$ represents optionally halogenated methyl.

A particularly preferred class of compounds of formula (I) are those wherein:

$R^1$ represents unsubstituted phenyl;

$R^2$ represents a methyl group which is substituted by a group $R^8$;

a straight- or branched-chain alkyl containing from one to three carbon atoms which is substituted by one or more halogen atoms; or a group selected from cyano, $-CHO$, $-CH=NOH$, $-CH=NOR^7$, $-CH=N-OCOCH_3$, $-CH=N-NHR^9$, $-COCH_3$, $-CH_2OH$ and $-CH(OH)CH_3$;

$R^3$ represents a phenyl ring substituted by one to three groups which may be the same or different selected from halogen or optionally halogenated methyl;

$R^4$ and $R^5$ represent methyl;

W represents $-NH-$;

$R^7$ represents methyl or ethyl;

$R^8$ represents a member of the group consisting of $-OH$, $-OR^7$, $-OCOCH_3$, $-N(CH_3)_2$, $-NHCH_3$, and $-S(O)_nCH_3$.

The following tabulated compounds also form part of the present invention, and in which Me means methyl, Et means ethyl, Ph means phenyl:

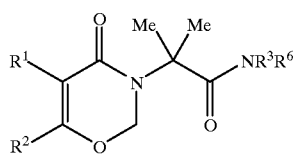

| Compound No. | $R^1$ | $R^2$ | $R^3$ | $R^6$ |
|---|---|---|---|---|
| 1 | Ph | $CH_2SO_2Me$ | 2,5-$F_2$ Ph | H |
| 2 | Ph | $CHF_2$ | 3-$CF_3$ Ph | H |
| 3 | Ph | $CH_2SMe$ | 2,5-$F_2$ Ph | H |
| 4 | Ph | $CH_2SMe$ | 3-$CF_3$ Ph | H |
| 5 | Ph | $CH_2SOMe$ | 2,5-$F_2$ Ph | H |
| 6 | Ph | $CH_2SOMe$ | 3-$CF_3$ Ph | H |
| 7 | Ph | $CH_2Br$ | 3-$CF_3$ Ph | H |
| 8 | Ph | $CH_2Br$ | 3-Cl Ph | H |
| 9 | Ph | $CH_2I$ | 3-Cl Ph | H |
| 10 | Ph | $CH_2SO_2Me$ | 3-$CF_3$ Ph | H |
| 11 | Ph | $CH_2SO_2Me$ | 3-Cl Ph | H |
| 12 | Ph | $CH_2SO_2Me$ | 2-F-5-$CF_3$ Ph | H |
| 13 | Ph | $CH_2Br$ | 2,5-$F_2$ Ph | H |
| 14 | Ph | $CH_2Br$ | 2-F-5-$CF_3$ Ph | H |
| 15 | Ph | $CH_2Br$ | 3,5-$Cl_2$ Ph | H |
| 16 | Ph | $CH_2Br$ | 2-F-5-Me Ph | H |
| 17 | Ph | $CHF_2$ | 2,5-$F_2$ Ph | H |
| 18 | Ph | $CHF_2$ | 3-Cl Ph | H |
| 19 | Ph | $CHF_2$ | 3-$CF_3$ Ph | H |
| 20 | Ph | $CHF_2$ | 2,5-$F_2$ Ph | H |
| 21 | Ph | $CHF_2$ | 2-F-5-$CF_3$ Ph | H |
| 22 | Ph | $CF_3$ | 3-$CF_3$ Ph | H |
| 23 | Ph | $CF_3$ | 2,5-$F_2$ Ph | H |
| 24 | Ph | $CH_2Cl$ | 3-$CF_3$ Ph | H |
| 25 | Ph | $CH_2Cl$ | 2,5-$F_2$ Ph | H |
| 26 | Ph | $CHBr_2$ | 3-Cl Ph | H |
| 27 | Ph | $CHCl_2$ | 3-$CF_3$ Ph | H |
| 28 | Ph | $CH_2I$ | 3-$CF_3$ Ph | H |
| 29 | Ph | $CH_2SCH_2CH_3$ | 3-$CF_3$ Ph | H |
| 30 | Ph | $CH_2OH$ | 3-Cl Ph | H |
| 31 | Ph | $CH_2OH$ | 3,5-$Cl_2$ Ph | H |
| 32 | Ph | $CH_2OH$ | 2-F-5-Me Ph | H |
| 33 | Ph | $CH_2OCH_3$ | 3-$CF_3$ Ph | H |
| 34 | Ph | $CH_2OCH_3$ | 3-Cl Ph | H |
| 35 | Ph | $CH_2OCH_3$ | 2,5-$F_2$ Ph | H |
| 36 | Ph | $CH_2OCH_3$ | 2-F-5-$CF_3$ Ph | H |
| 37 | Ph | $CH_2OCH_2CH_3$ | 3-$CF_3$ Ph | H |
| 38 | Ph | $CH_2OCHF_2$ | 2-F-5-$CF_3$ Ph | H |
| 39 | Ph | $CH_2OCHF_2$ | 3-$CF_3$ Ph | H |
| 40 | Ph | $CH_2OCF_3$ | 3-$CF_3$ Ph | H |
| 41 | Ph | $CH_2SCF_3$ | 3-$CF_3$ Ph | H |
| 42 | Ph | $CH_2OCH_2CF_3$ | 3-$CF_3$ Ph | H |
| 43 | Ph | $CH_2OC(O)CH_3$ | 2-F,5-$CF_3$ Ph | H |
| 44 | Ph | $CH(OH)CH_3$ | 2,5-$F_2$ Ph | H |
| 45 | Ph | $CH(OH)CH_3$ | 3-$CF_3$ Ph | H |
| 46 | Ph | $CH=CH_2$ | 2-F-5-$CF_3$ Ph | H |
| 47 | Ph | $CH=CH_2$ | 3-$CF_3$ Ph | H |
| 48 | Ph | $CH=CHCH_3$ | 3-Cl Ph | H |
| 49 | Ph | $CH=NOH$ | 3-$CF_3$ Ph | H |
| 50 | Ph | $CH=NOC(O)CH_3$ | 3-$CF_3$ Ph | H |
| 51 | Ph | $CH=NNH_2$ | 2,5-$F_2$ Ph | H |
| 52 | Ph | $CH=NNH_2$ | 3-$CF_3$ Ph | H |
| 53 | Ph | $CH=NNH_2$ | 3-Cl Ph | H |
| 54 | Ph | $CH=NNHMe$ | 3-$CF_3$ Ph | H |
| 55 | Ph | $CN$ | 2,5-$F_2$ Ph | H |
| 56 | Ph | $CH_2CN$ | 3-$CF_3$ Ph | H |
| 57 | Ph | $CH_2CN$ | 2,5-$F_2$ Ph | H |
| 58 | Ph | $CH_2CN$ | 3-Cl Ph | H |
| 59 | Ph | $CH_2CN$ | 2-F-5-$CF_3$ Ph | H |
| 60 | Ph | $CO_2H$ | 3-$CF_3$ Ph | H |
| 61 | Ph | $CO_2Me$ | 2,5-$F_2$ Ph | H |
| 62 | Ph | $CO_2CH_2CH_3$ | 3-Cl Ph | H |
| 63 | Ph | $CONH_2$ | 2-F-5-$CF_3$ Ph | H |
| 64 | Ph | $CONHMe$ | 3-$CF_3$ Ph | H |
| 65 | Ph | $CONMe_2$ | 2,5-$F_2$ Ph | H |
| 66 | Ph | $CH=O$ | 3-Cl Ph | H |
| 67 | Ph | $CH_2SO_2Me$ | 2-F-5-$CF_3$ Ph | H |
| 68 | 2-F Ph | $CHF_2$ | 3-$CF_3$ Ph | H |
| 69 | 2-F Ph | $CH_2SMe$ | 2,5-$F_2$ Ph | H |
| 70 | 2-F Ph | $CH_2SOMe$ | 3-Cl Ph | H |
| 71 | 2-F Ph | $CH_2Br$ | 2-F-5-$CF_3$ Ph | H |
| 72 | 2-F Ph | $CH_2F$ | 3-$CF_3$ Ph | H |
| 73 | 2-F Ph | $CH_2Cl$ | 2,5-$F_2$ Ph | H |
| 74 | 2-F Ph | $CHCl_2$ | 3-Cl Ph | H |
| 75 | 2-F Ph | $CH_2I$ | 2-F-5-$CF_3$ Ph | H |
| 76 | 2-F Ph | $CH_2SO_2Me$ | 3-$CF_3$ Ph | H |
| 77 | 2-F Ph | $CH_2OH$ | 2,5-$F_2$ Ph | H |
| 78 | 2-F Ph | $CH_2OMe$ | 3-Cl Ph | H |

| | | | | |
|---|---|---|---|---|
| 79 | 2-F Ph | CH$_2$OCHF$_2$ | 2-F-5-CF$_3$ Ph | H |
| 80 | 2-F Ph | CH$_2$OCF$_3$ | 3-CF$_3$ Ph | H |
| 81 | 2-F Ph | CH(OH)CH$_3$ | 2,5-F$_2$ Ph | H |
| 82 | 2-F Ph | CH=CH$_2$ | 3-Cl Ph | H |
| 83 | 2-F Ph | CH$_2$CN | 3-CF$_3$ Ph | H |
| 84 | 2-F Ph | CH=O | 2,5-F$_2$ Ph | H |
| 85 | 2-Cl Ph | CH$_2$SO$_2$Me | 3-CF$_3$ Ph | H |
| 86 | 2-Cl Ph | CHF$_2$ | 2,5-F$_2$ Ph | H |
| 87 | 2-Cl Ph | CH$_2$SMe | 3-Cl Ph | H |
| 88 | 2-Cl Ph | CH$_2$SOMe | 3-CF$_3$ Ph | H |
| 89 | 2-Cl Ph | CH$_2$Br | 3-CF$_3$ Ph | H |
| 90 | 2-Cl Ph | CH$_2$F | 2,5-F$_2$ Ph | H |
| 91 | 2-Cl Ph | CH$_2$Cl | 3-Cl Ph | H |
| 92 | 2-Cl Ph | CHCl$_2$ | 3-CF$_3$ Ph | H |
| 93 | 2-Cl Ph | CH$_2$I | 3-CF$_3$ Ph | H |
| 94 | 2-Cl Ph | CH$_2$SO$_2$Me | 2,5-F$_2$ Ph | H |
| 95 | Ph | oxiranyl | 3-CF$_3$ Ph | H |
| 96 | Ph | oxiranyl | 2,5-F$_2$ Ph | H |
| 97 | Ph | oxiranyl | 3-Cl Ph | H |
| 98 | Ph | oxiranyl | 2-F-5-CF$_3$ Ph | H |
| 99 | Ph | CH$_2$SMe | 3,5-Cl$_2$ Ph | H |
| 100 | Ph | CH$_2$SCH$_2$CH$_3$ | 3,5-Cl$_2$ Ph | H |
| 101 | Ph | CH$_2$SCH$_2$CH$_3$ | 3-CF$_3$ Ph | H |
| 102 | Ph | CH$_2$OH | 3-CF$_3$ Ph | H |
| 103 | Ph | CH$_2$OC(O)CH$_3$ | 3-CF$_3$ Ph | H |
| 104 | Ph | CH$_2$OC(O)CH$_3$ | 3,5-Cl$_2$ Ph | H |
| 105 | Ph | CH$_2$NHMe | 3-CF$_3$ Ph | H |
| 106 | Ph | CH$_2$NMe$_2$ | 3-CF$_3$ Ph | H |
| 107 | Ph | CH$_2$NMe$_2$ | 3,5-Cl$_2$ Ph | H |
| 108 | Ph | CH$_2$NHMe | 3,5-Cl$_2$ Ph | H |
| 109 | Ph | CH=O | 3,5-Cl$_2$ Ph | H |
| 110 | Ph | CH$_2$OC(O)CH$_3$ | 2,5-F$_2$ Ph | H |
| 111 | Ph | CH$_2$OMe | 3,5-Cl$_2$ Ph | H |
| 112 | Ph | CH$_2$F | 3,5-Cl$_2$ Ph | H |
| 113 | Ph | CH$_2$F | 2,5-F$_2$ Ph | H |
| 114 | Ph | CH$_2$Cl | 3,5-Cl$_2$ Ph | H |
| 115 | Ph | CH=NOH | 3,5-Cl$_2$ Ph | H |
| 116 | Ph | CH=NOEt | 3,5-Cl$_2$ Ph | H |
| 117 | Ph | CH=NOMe | 3,5-Cl$_2$ Ph | H |
| 118 | Ph | CH=N—OC(O)CH$_3$ | 3,5-Cl$_2$ Ph | H |
| 119 | Ph | CH=NNH$_2$ | 3,5-Cl$_2$ Ph | H |
| 120 | Ph | CN | 3,5-Cl$_2$ Ph | H |
| 121 | Ph | CH=NNHMe | 3,5-Cl$_2$ Ph | H |
| 122 | Ph | CH$_2$OMe | 2-Cl-5-Me Ph | H |
| 123 | Ph | CH(OH)Me | 3,5-Cl$_2$ Ph | H |
| 124 | Ph | CH$_2$OMe | 2-Me-5-Cl Ph | H |
| 125 | Ph | CH$_2$OCH$_2$CH$_3$ | 2,5-F$_2$ Ph | H |
| 126 | Ph | CH$_2$OCH$_2$CH$_3$ | 3,5-Cl$_2$ Ph | H |
| 127 | Ph | COMe | 3,5-Cl$_2$ Ph | H |
| 128 | Ph | CH=NOMe | 2,5-F$_2$ Ph | H |
| 129 | Ph | CH=O | 2,5-F$_2$ Ph | H |
| 130 | Ph | CH$_2$OH | 2,5-F$_2$ Ph | H |
| 131 | Ph | CH$_2$F | 2-F-5-CF$_3$ Ph | H |
| 132 | Ph | CH$_2$F | 3,4,5-F$_3$ Ph | H |
| 133 | Ph | CH$_2$F | 3,5-F$_2$ Ph | H |
| 134 | Ph | CH$_2$F | 2-Cl-3,5-F$_2$ Ph | H |
| 135 | Ph | CH$_2$F | 3-CF$_3$ Ph | H |
| 136 | Ph | CH$_2$F | 3-Cl Ph | H |
| 137 | Ph | CH$_2$CH$_2$CH$_2$Cl | 3,5-Cl$_2$ Ph | H |
| 138 | Ph | CH$_2$CH$_2$CH$_2$Cl | 3-Cl Ph | H |
| 139 | Ph | CH$_2$CH$_2$CH$_2$Cl | 3-CF$_3$ Ph | H |
| 140 | Ph | CH$_2$CH$_2$CH$_2$Cl | 2,5-F$_2$ Ph | H |
| 141 | Ph | CHBr$_2$ | 3-Cl Ph | H |

The following compounds from the above Table are preferred:

N-(2,5-difluorophenyl)-2-(2,3-dihydro-6-methylsulphonylmethyl-4-oxo-5-phenyl-4H-1,3-oxazin-3-yl)-2-methylpropanamide N-(2,5-difluorophenyl)-2-(2,3-dihydro-6-methylthiomethyl-4-oxo-5-phenyl-4H-1,3-oxazin-3-yl)-2-methylpropanamide N-(3-trifluoromethylphenyl)-2-(2,3-dihydro-6-methylthiomethyl-4-oxo-5-phenyl-4H-1,3-oxazin-3-yl)-2-methylpropanamide N-(3-trifluoromethylphenyl)-2-(6-difluoromethyl-2,3-dihydro-4-oxo-5-phenyl-4H-1,3-oxazin-3-yl)-2-methylpropanamide N-(3,5-dichlorophenyl)-2-(6-bromomethyl-2,3-dihydro-4-oxo-5-phenyl-4H-1,3-oxazin-3-yl)-2-methylpropanamide N-(2,5-difluorophenyl)-2-(6-bromomethyl-2,3-dihydro-4-oxo-5-phenyl-4H-1,3-oxazin-3-yl)-2-methylpropanamide N-(3,5-dichlorophenyl)-2-(2,3-dihydro-6-methoxymethyl-4-oxo-5-phenyl-4H-1,3-oxazin-3-yl)-2-methylpropanamide N-(2,5-difluorophenyl)-2-(2,3-dihydro-6-methoxymethyl-4-oxo-5-phenyl-4H-1,3-oxazin-3-yl)-2-methylpropanamide N-(3-trifluoromethylphenyl)-2-(2,3-dihydro-6-methoxymethyl-4-oxo-5-phenyl-4H-1,3-oxazin-3-yl)-2-methylpropanamide N-(3,5-dichlorophenyl)-2-(6-fluoromethyl-2,3-dihydro-4-oxo-5-phenyl-4H-1,3-oxazin-3-yl)-2-methylpropanamide N-(2,5-difluorophenyl)-2-(6-fluoromethyl-2,3-dihydro-4-oxo-5-phenyl-4H-1,3-oxazin-3-yl)-2-methylpropanamide N-(2,5-difluorophenyl)-2-(6-chloromethyl-2,3-dihydro-4-oxo-5-phenyl-4H-1,3-oxazin-3-yl)-2-methylpropanamide N-(3,5-dichlorophenyl)-2-(6-chloromethyl-2,3-dihydro-4-oxo-5-phenyl-4H-1,3-oxazin-3-yl)-2-methylpropanamide N-(3-trifluorophenyl)-2-(6-chloromethyl-2,3-dihydro-4-oxo-5-phenyl-4H-1,3-oxazin-3-yl)-2-methylpropanamide N-(5-chloro-2-methylphenyl)-2-(2,3-dihydro-6-methoxymethyl-4-oxo-5-phenyl-4H-1,3-oxazin-3-yl)-2-methylpropanamide N-(3-chlorophenyl)-2-(2,3-dihydro-6-methoxymethyl-4-oxo-5-phenyl-4H-1,3-oxazin-3-yl)-2-methylpropanamide N-(2-fluoro-5-trifluoromethylphenyl)-2-(2,3-dihydro-6-methoxymethyl-4-oxo-5-phenyl-4H-1,3-oxazin-3-yl)-2-methylpropanamide N-(2,5-difluorophenyl)-2-(6-ethoxymethyl-2,3-dihydro-4-oxo-5-phenyl-4H-1,3-oxazin-3-yl)-2-methylpropanamide N-(3-trifluoromethylphenyl)-2-(6-ethoxymethyl-2,3-dihydro-4-oxo-5-phenyl-4H-1,3-oxazin-3-yl)-2-methylpropanamide N-(3,5-dichlorophenyl)-2-(6-ethoxymethyl-2,3-dihydro-4-oxo-5-phenyl-4H-1,3-oxazin-3-yl)-2-methylpropanamide N-(2-fluoro-5-trifluoromethylphenyl)-2-(6-fluoromethyl-2,3-dihydro-4-oxo-5-phenyl-4H-1,3-oxazin-3-yl)-2-methylpropanamide N-(3,4,5-trifluorophenyl)-2-(6-fluoromethyl-2,3-dihydro-4-oxo-5-phenyl-4H-1,3-oxazin-3-yl)-2-methylpropanamide N-(3,5-difluorophenyl)-2-(6-fluoromethyl-2,3-dihydro-4-oxo-5-phenyl-4H-1,3-oxazin-3-yl)-2-methylpropanamide N-(2-chloro-3,5-difluorophenyl)-2-(6-fluoromethyl-2,3-dihydro-4-oxo-5-phenyl-4H-1,3-oxazin-3-yl)-2-methylpropanamide N-(3-trifluoromethylphenyl)-2-(6-fluoromethyl-2,3-dihydro-4-oxo-5-phenyl-4H-1,3-oxazin-3-yl)-2-methylpropanamide N-(3-chlorophenyl)-2-(6-fluoromethyl-2,3-dihydro-4-oxo-5-phenyl-4H-1,3-oxazin-3-yl)-2-methylpropanamide N-(3,5-dichlorophenyl)-2-[6-(3-chloropropyl)-2,3-dihydro-4-oxo-5-phenyl-4H-1,3-oxazin-3-yl)-2-methylpropanamide N-(3-chlorophenyl-2-[6-(3-chloropropyl)-2,3-dihydro-4-oxo-5-phenyl-4H-1,3-oxazin-3-yl]-2-methylpropanamide N-(3-trifluoromethylphenyl)-2-(6-(3-chloropropyl)-2,3-dihydro-4-cxo-5-phenyl-4H-1,3-oxazin-3-yl]-2-methylpropanamide N-(2,5-difluorophenyl)-2-[6-(3-chloropropyl)-2,3-dihydro-4-oxo-5-phenyl-4H-1,3-oxaz in-3-yl]-2-methylpropanamide N-(2,5-difluorophenyl)-2-(2,3-dihydro-6-methylsulphinylmethyl-4-oxo-5-phenyl-4H-1,3-oxazin-3-yl)-2-methylpropanamide N-(3-trifluoromethylphenyl)-2-(2,3-dihydro-6-methylsulphinylmethyl-4-oxo-5-phenyl-4H-1,3-oxazin-3-yl)-2-methyl-propanamide N-(3-chlorophenyl)-2-(2,3-dihydro-6-iodomethyl-4-oxo-5-phenyl-4H-1,3-oxazin-3-yl)-2-methylpropanamide N-(3-chlorophenyl)-2-(6-bromomethyl-2,3-dihydro-4-oxo-5-phenyl-4H-1,3-oxazin-3-yl)-2-methylpropanamide N-(3-trifluoromethylphenyl)-2-(6-bromomethyl-2,3-dihydro-4-oxo-5-phenyl-4H-1,3-oxazin-3-yl)-2-methylpropanamide N-(3-chlorophenyl)-2-(6-dibromomethyl-2,3-dihydro-4-oxo-5-phenyl-4H-1,3-oxazin-3-yl)-2-methylpropanamide N-(3,5-dichlorophenyl-2-(2,3-dihydro-6-methylthiomethyl-4-oxo-5-phenyl-4H-1,3-oxazin-3-yl)-2-methylpropanamide N-(3,5-dichlorophenyl)-2-(6-ethylthiomethyl-2,3-dihydro-4-oxo-5-phenyl-4H-1,3-oxazin-3-yl)-2-methylpropanamide N-(3-trifluoromethylphenyl)-2-(6-ethylthiomethyl-2,3-dihydro-4-oxo-5-phenyl-4H-1,3-oxazin-3-yl)-2-methylpropanamide N-(3-trifluoromethylphenyl)-2-(2,3-dihydro-6-hydroxymethyl-4-oxo-5-phenyl-4H-1,3-oxazin-3-yl)-2-methylpropanamide N-(3,5-dichlorophenyl)-2-(2,3-dihydro-6-hydroxymethyl-4-oxo-5-phenyl-4H-1,3-oxazin-3-yl)-2-methylpropanamide N-(2,5-difluorophenyl)-2-(2,3-dihydro-6-hydroxymethyl-4-oxo-5-phenyl-4H-1,3-oxazin-3-yl)-2-methylpropanamide N-(3-trifluoromethylphenyl)-2-(6-acetoxymethyl-2,3-dihydro-4-oxo-5-phenyl-4H-1,3-oxazin-3-yl)-2-methylpropanamide N-(3,5-dichlorophenyl)-2-(6-acetoxymethyl-2,3-dihydro-4-oxo-5-phenyl-4H-1,3-oxazin-3-yl)-2-methylpropanamide N-(3-trifluoromethylphenyl)-2-(2,3-dihydro-6-methylaminomethyl-4-oxo-5-phenyl-4H-1,3-oxazin-3-yl)-2-methylpropanamide N-(3-trifluoromethylphenyl)-2-(2,3-dihydro-6-dimethylaminomethyl-4-oxo-5-phenyl-4H-1,3-oxazin-3-yl)-2-methylpropanamide N-(3,5-dichlorophenyl)-2-(2,3-dihydro-6-dimethylaminomethyl-4-oxo-5-phenyl-4H-1,3-oxazin-3-yl)-2-methylpropanamide N-(3,5-dichlorophenyl)-2-(2,3-dihydro-6-methylaminomethyl-4-oxo-5-phenyl-4H-1,3-oxazin-3-yl)-2-methylpropanamide N-(3,5-dichlorophenyl)-2-(2,3-dihydro-6-formyl-4-oxo-5-phenyl-4H-1,3-oxazin-3-yl)-2-methylpropanamide N-(3,5-dichlorophenyl)-2-(6-acetyl-2,3-dihydro-4-oxo-5-phenyl-4H-1,3-oxazin-3-yl)-2-methylpropanamide N-(2,5-difluorophenyl)-2-(6-acetoxymethyl-2,3-dihydro-4-oxo-5-phenyl-4H-1,3-oxazin-3-yl)-2-methylpropanamide N-(2-chloro-5-methylphenyl)-2-(2,3-dihydro-6-methoxymethyl-4-oxo-5-phenyl-4H-1,3-oxazin-3-yl)-2-methylpropanamide N-(3,5-dichlorophenyl)-2-(2,3-dihydro-6-hydroxyiminomethylene-4-oxo-5-phenyl-4H-1,3-oxazin-3-yl)-2-methylpropanamide N-(3,5-dichlorophenyl)-2-(6-ethoxyiminomethylene-2,3-dihydro-4-oxo-5-phenyl-4H-1,3-oxazin-3-yl)-2-methylpropanamide N-(3,5-dichlorophenyl)-2-(2,3-dihydro-6-methoxyiminomethylene-4-oxo-5-phenyl-4H-1,3-oxazin-3-yl)-2-methylpropanamide N-(2,5-difluorophenyl)-2-(2,3-dihydro-6-methoxyiminomethylene-4-oxo-5-phenyl-4H-1,3-oxazin-3-yl)-2-methylpropanamide N-(3,5-dichlorophenyl)-2-(6-acetoxyiminomethylene-2,3-dihydro-4-oxo-5-phenyl-4H-1,3-oxazin-3-yl)-2-methylpropanamide N-(3,5-dichlorophenyl)-2-(6-aminoiminomethylene-2,3-dihydro-4-oxo-5-phenyl-4H-1,3-oxazin-3-yl)-2-methylpropanamide N-(3,5-dichlorophenyl)-2-(2,3-dihydro-6-methylaminoiminomethylene-4-oxo-5-phenyl-4H-1,3-oxazin-3-yl)-2-methylpropanamide N-(3,5-dichlorophenyl)-2-(6-cyano-2,3-dihydro-4-oxo-5-phenyl-4H-1,3-oxazin-3-yl)-2-methylpropanamide N-(3,5-dichlorophenyl)-2[2,3-dihydro-6-(1-hydroxyethyl)-4-oxo-5-phenyl-4H-1,3-oxazin-3-yl]-2-methylpropanamide, and N-(2,5-difluorophenyl)-2-(2,3-dihydro-6-formyl-4-oxo-5-phenyl-4H-1,3-oxazin-3-yl)-2-methylpropanamide.

Compounds of formula (I) above may be prepared by the application or adaptation on known methods (i.e. methods heretofore used or described in the literature).

It is to be understood that in the descriptions of the following processes the sequences may be performed in different orders, and that suitable protecting groups may be required to achieve the compounds sought.

According to a feature of the present invention compounds of formula (I) may be prepared by the reaction of a compound of formula (II):

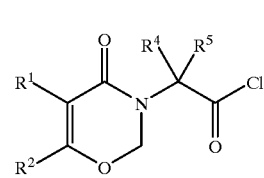

(II)

wherein $R^1$, $R^2$, $R^4$ and $R^5$ are as defined above, with an amine of formula (III):

$R^6NH—R^3$ (III)

wherein $R^3$ and $R^6$ are as defined above. The reaction is generally performed in the presence of a base, for example a tertiary amine such as triethylamine and in an inert solvent such as dichloromethane at a temperature from 0° C. to the reflux temperature of the solvent.

According to a further feature of the present invention compounds of formula (I) in which $R^2$ represents 3-chloropropyl may be prepared by reaction of a compound of formula (IV):

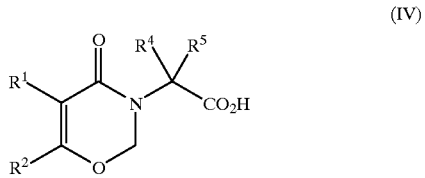

(IV)

in which $R^1$, $R^4$ and $R^5$ are as defined above and $R^2$ is replaced by cyclopropyl, with a chlorinating agent followed by reaction of an amine of formula (III). The reaction may be performed according to the conditions described in the above process. In this modification the acidic conditions of the chlorination reaction result in conversion of the cyclopropyl group R into the 3-chloropropyl compound.

According to a further feature of the present invention compounds of formula (I) in which $R^1$, $R^2$, $R^3$, $R^4$, and $R^5$ are as defined above and W represents —NH— may be prepared by the reaction of the corresponding compound of formula (V):

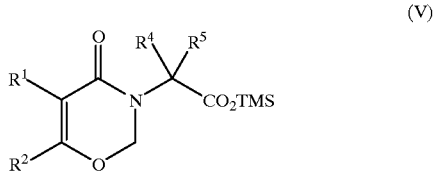

(V)

in which $R^1$, $R^2$, $R^4$, $R^5$ are defined above and TMS is trimethylsilyl, with a chlorinating agent for example oxalyl chloride to form a compound of formula (II) in situ which is subsequently reacted with an amine of formula (III) according to the above described process. This procedure is useful for preparation of the intermediate (II) under non acidic conditions as is described in J. Organic Chemistry (1978), Vol.43, pages 3972–3974.

According to a further feature of the present invention compounds of formula (I) in which W is $NR^6$ and $R^6$ is hydrogen, lower alkyl, haloalkyl, alkenyl or alkynyl may also be prepared by the reaction of a compound of formula (IV) above wherein $R^1$, $R^2$, $R^4$ and $R^5$ are as defined above, with an amine of formula (III) above wherein $R^3$ is as defined above and in which $R^6$ is hydrogen, lower alkyl, haloalkyl, alkenyl or alkynyl, in the presence of a coupling reagent, for example N,N'-dicyclohexylcarbodiimide, optionally in the presence of a base, for example 4-dimethylaminopyridine, and in an inert solvent such as dichloromethane at a temperature from 0 to 60° C.

According to a further feature of the present invention compounds of formula (I) wherein $R^6$ represents a hydrogen atom and $R^1$, $R^2$, $R^3$, $R^4$ and $R^5$ are as hereinbefore defined, may also be prepared by the reaction of a carboxylic acid of formula (IV) above with a phenyl carbamate of formula $PhO_2C$—$NHR^3$, wherein $R^3$ is as defined above in the presence of a base, preferably 1,8-diazabicyclo[5.4.0] undec-7-ene, in an inert solvent (for example 1,4-dioxan) and at a temperature from 20 to 100° C.

Compounds of formula (I) wherein W is $NR^6$ and $R^6$ represents a hydrogen atom may also be prepared by the reaction of a trimethylsilylester of formula (V) above wherein $R^1$, $R^2$, $R^4$ and $R^5$ are as defined above, and TMS means trimethylsilyl, with an amine of formula —$NH_2R^3$, wherein $R^3$ is as defined above.

The reaction is generally performed in the presence of a catalytic amount of a titanium (IV) salt, preferably prepared in situ from the reaction of titanium (IV) chloride and silver (I) trifluoromethanesulphonate, and in the presence of an anhydride preferably 4-trifluoromethylbenzoic anhydride and in an inert solvent for example dichloromethane at a temperature from 0 to 60° C. This procedure is useful for weakly nucleophilic amines and is described in Chem. Letters (1993), 1053–1054 by M. Miyashita, I. Shirna and T. Mukaiyama.

Compounds of formula (I) may be prepared by interconversion from other compounds of formula (I), for example as described below.

According to a further feature of the present invention compounds of formula (I) in which $R^2$ is —CHO may be prepared by oxidation of the corresponding compounds of formula (I) in which $R^2$ is —$CH_2OH$ using for example pyridinium chlorochromate in dichloromethane at 0° C. to the reflux temperature.

According to a further feature of the present invention compounds of formula (I) in which $R^1$, $R^3$, $R^4$, $R^5$ and W are as defined above and $R^2$ represents —$COR^7$ may be prepared by oxidation of the corresponding compounds of formula (I) in which $R^2$ is —$CH(OH)R^7$, using for example pyridinium chlorochromate in dichloromethane at 0° C. to the reflux temperature.

According to a further feature of the present invention compounds of formula (I) in which $R^2$ is an oxiranyl group may be prepared by the reaction of the corresponding compound of formula (I) in which $R^2$ is —CHO with a methylene transfer reagent, preferably dimethylsulfoxonium methylide in a solvent, preferably dimethyl sulphoxide (DMSO), at a temperature of from 10 to 60° C.

According to a further feature of the present invention compounds of formula (I) in which $R^2$ represents alkenyl optionally substituted by halogen and wherein the double bond is located between the two carbon atoms closest to the 1,3-oxazin-4-one ring may be prepared by reaction of the corresponding compound of formula I in which $R^2$ is —CHO or —$COR^7$ with a phosphorane, typically generated by reaction of a phosphonium salt of formula $Ph_3P^+$ $CHR^{11}R^{11a}Y^-$, in which Y represents chlorine, bromine or iodine, $R^{11}$ and $R^{11a}$ represent hydrogen or optionally halogenated alkyl containing from one to eight carbon atoms with the proviso that the total number of carbon atoms in the combined alkyl groups $R^7$, $R^{11}$ and $R^{11a}$ does not exceed eight. The reaction is generally performed in the presence of a strong base e.g. n-butyl lithium and in an inert solvent e.g. tetrahydrofuran at a temperature from 0° C. to the reflux temperature, the reaction being conducted under an inert atmosphere.

According to a further feature of the present invention compounds of formula (I) in which $R^2$ is —$CH(OH)R^{12}$ wherein $R^{12}$ represents a $C_1$–$C_9$ alkyl group may be prepared by reaction of the corresponding compound of formula (I) in which $R^2$ represents —CHO with a Grignard reagent of formula $R^{12}Mg-X$ wherein $R^{12}$ is as defined above and X represents a bromine or iodine. The reaction may be performed in an inert solvent e.g. ether or tetrahydrofuran at a temperature from 20 to 60° C.

According to a further feature of the present invention compounds of formula (I) in which $R^2$ is $-CH_2OH$ may be prepared by the hydrolysis of the corresponding compound of formula (I) in which $R^2$ is $-CH_2OC(O)R^7$ wherein $R^7$ is as defined above. Preferably $R^7$ is methyl, and the hydrolysis is performed using a base e.g. potassium carbonate in an aqueous alcohol solution at 0 to 50° C.

According to a further feature of the present invention compounds of formula (I) in which $R^2$ is difluoromethyl may be prepared by reaction of the corresponding compound of formula (I) in which $R^2$ is $-CHO$ with diethylaminosulphur trifluoride in an inert solvent, e.g. dichloromethane, at a temperature of 0 to 60° C.

According to a further feature of the present invention compounds of formula (I) in which $R^2$ is $-CF_2R^7$ may be prepared by reaction of the corresponding compound of formula (I) in which $R^2$ is $-COR^7$ with diethylaminosulphur trifluoride in an inert solvent, e.g. dichloromethane, at a temperature of 0 to 60° C.

According to a further feature of the present invention compounds of formula I in which $R^2$ is $-CH_2I$ may be prepared by the reaction of the corresponding compound of formula I wherein $R^2$ is $-CH_2Br$ or $-CH_2Cl$. The reaction is performed using sodium or potassium iodide in a inert solvent preferably acetone at a temperature from ambient to the reflux temperature of the solvent.

According to a further feature of the present invention compounds of formula (I) wherein $R^2$ is $C(Z)R^{12a}R^{12b}$, Z represents bromine, chlorine or iodine and $R^{12a}$ and $R^{12b}$ represent hydrogen or an optionally halogenated alkyl group containing up to nine carbon atoms, with the proviso that the total number of carbon atoms in the combined alkyl groups $R^{12a}$ and $R^{12b}$ does not exceed nine may be prepared by reaction of the corresponding compound of formula (I) in which $R^2$ is $-CHR^{12a}R^{12b}$ with a halogenating agent, preferably N-bromosuccinimide, N-chlorosuccinimide and N-iodosuccinimide in an inert solvent e.g. tetrachloromethane, optionally in the presence of a radical initiator e.g. azobis-isobutyronitrile or by irradiation with a tungsten light source, and at a temperature from ambient to the reflux temperature of the solvent.

According to a further feature of the present invention compounds of formula (I) wherein $R^2$ represents a $C_1$ to $C_{10}$ alkyl group substituted by a group $-SR^7$, may be prepared by the reaction of the corresponding compound of formula (I) in which the $-SR^7$ group is replaced by a leaving group, preferably chloro or bromo, with a thiol of formula $R^7SH$ or alkali metal salt of the thiol $R^7SM$ wherein M represents lithium or sodium. The reaction is performed in an inert solvent e.g. N,N-dimethylformamide at a temperature from 0 to 60° C.

According to a further feature of the present invention compounds of formula (I) wherein $R^2$ represents a $C_1$ to $C_{10}$ alkyl group substituted by $-OC(O)R^7$ wherein $R^7$ is as defined above may be prepared by reaction of the corresponding compound of formula (I) in which the $-OC(O)R^7$ group is replaced by a leaving group, with a salt of formula $R^7-CO_2^-M_1^+$, wherein $M_1$ represents sodium or potassium. The leaving group is preferably chlorine or bromine. The reaction is typically performed in an inert solvent preferably N,N-dimethylformamide at a temperature from ambient to 120° C.

According to a further feature of the present invention compounds of formula (I) in which $R^2$ represents $-CO_2R^7$ may be prepared by esterification of the corresponding compound of formula (I) in which $R^2$ is $-CO_2H$, to replace the hydrogen atom with a group $R^7$. The reaction is preferably performed with an alcohol of formula $R^7OH$ and diethylazodicarboxylate in an inert solvent e.g. ether at a temperature from 0° C. to the reflux temperature of the solvent. Alternatively, the conversion may be performed by chlorination of the corresponding compound of formula (I) in which $R^2$ is $-CO_2H$ using for example oxalyl chloride, in an inert solvent, e.g. dichloromethane or 1,2-dichlorethane, optionally in the presence of a catalyst such as N,N-dimethylformamide at a temperature from 20° C. to the reflux temperature of the mixture to give the corresponding acid chloride, which is subsequently reacted with an alcohol of formula $R^7OH$ in an inert solvent e.g. tetrahydrofuran at a temperature from 0° C. to the reflux temperature of the solvent.

According to a further feature of the present invention compounds of formula (I) wherein $R^2$ represents a $C_1$ to $C_{10}$ alkyl group substituted by $-OR^7$ wherein $R^7$ is as defined above, may be prepared by reaction of the corresponding compound of formula (I) in which $-OR^7$ is replaced by a hydroxy group, with an alkyl halide, preferably iodide of formula $R^7-I$. The reaction is generally performed in the presence of silver (I) oxide and in an inert solvent e.g. acetonitrile at a temperature from ambient to the reflux temperature or optionally in the presence of a weak base, for example potassium carbonate. The general procedure is described in J. Org. Chem. 40, 206 (1975). Compounds of formula (I) in which $R^2$ represents a $C_1-C_{10}$ alkyl group substituted by $-OR^7$ may also be prepared by reaction of the corresponding compound of formula (I) in which $-OR^7$ is replaced by a hydroxy group, with an alcohol of formula $R^7OH$ in the presence of a trialkylphosphine, e.g. tri-n-butylphosphine and 1,1'-(azodicarbonyl)piperidine, in an inert solvent (e.g. toluene at a temperature from 20° C. to the reflux temperature). The reaction is described by J. R. Falck in Tetrahedron Letters 35, 5997 (1994).

According to a further feature of the present invention compounds of formula (I) in which $R^2$ is $-CH=N-OH$ may be prepared by reaction of the corresponding compound of formula (I) in which $R^2$ is $-CHO$ with hydroxylamine hydrochloride in the presence of a weak base (e.g. sodium acetate) in an inert solvent (e.g. ethanol) at a temperature from ambient to the reflux temperature of the solvent.

According to a further feature of the present invention compounds of formula (I) in which $R^2$ is $-CH=N-OR^7$, wherein $R^7$ is as defined above may be prepared by reaction of the corresponding compound of formula (I) in which $R^2$ is $-CHO$ with an O-alkylhydroxylamine of formula $R^7O-NH_2$ which may be in the form of salt e.g. the hydrochloride salt in the presence of a weak base (e.g. sodium acetate) in an inert solvent (e.g. ethanol) at a temperature from ambient to the reflux temperature of the solvent.

According to a further feature of the present invention compounds of formula (I) in which $R^2$ is $-CH=N-OCOR^7$ wherein $R^7$ is as defined above, may be prepared by reaction of the corresponding compound of formula (I) in which $R^2$ is $-CH=N-OH$ with an acid chloride of formula $R^7COCl$ in an inert solvent e.g. tetrahydrofuran at a temperature from 0° C. to the reflux temperature of the solvent.

According to a further feature of the present invention compounds of formula (I) in which $R^2$ is $-CH=N-NR^9R^{10}$ may be prepared by reaction of the corresponding compound of formula (I) in which $R^2$ is $-CHO$ with a hydrazine of formula $R^9R^{10}N-NH_2$ in an inert solvent (e.g.

ethanol) at a temperature from 20° C. to the reflux temperature of the solvent.

According to a further feature of the present invention, compounds of formula (I) in which $R^2$ is cyano may be prepared by dehydration of the corresponding compound of formula (I) in which $R^2$ is —CH=N—OH. The reaction may be performed by reaction with trifluoroacetic anhydride, acetic anhydride or phosphorus oxychloride at a temperature from 20° C. to the reflux temperature of the mixture. The dehydration may also be performed according to the procedure described in Synthesis (1983), page 741, by reaction with copper (II) acetate in a mixture of acetonitrile and water, and at a temperature from 20° C. to the reflux temperature of the mixture.

According to a further feature of the present invention thiol esters of formula (I) in which $R^2$ is —$COSR^7$ and $R^7$ is as defined above may be prepared by chlorination of the corresponding compound of formula (I) in which $R^2$ is —$CO_2H$ using a chlorinating agent (e.g. oxalyl chloride) in an inert solvent (e.g. dichloromethane or 1,2-dichloroethane) optionally in the presence of a catalyst such as N,N-dimethylformamide at a temperature from 20° C. to the reflux temperature of the mixture to give the corresponding acid chloride, which is subsequently reacted with a thiol of formula $R^7SH$ wherein $R^7$ is as defined above in an inert solvent e.g. tetrahydrofuran at a temperature from 0° C. to the reflux temperature of the solvent.

According to a further feature of the present invention, compounds of formula (I) in which $R^2$ is —$CH_2F$ may be prepared by reaction of the corresponding compound of formula I in which $R^2$ is —$CH_2OH$ with diethylaminosulphur trifluoride in an inert solvent e.g. dichloromethane at a temperature from 0 to 60° C.

According to a further feature of the present invention compounds of formula (I) in which $R^2$ is —$CHFR^7$ may be prepared by reaction of the corresponding compound of formula (I) in which R is —$CH(OH)R^7$ with diethylaminosulphur trifluoride in an inert solvent, e.g. dichloromethane at a temperature from 0 to 60° C.

According to a further feature of the present invention, compounds of formula (I) in which $R^2$ is —$CONR^9R^{10}$ wherein $R^9$ and $R^{10}$ are as defined above may be prepared by reaction of the corresponding compound of formula (I) in which $R^2$ is —$CO_2H$ with a chlorinating agent to produce the carboxylic acid chloride by the method described above, which is subsequently reacted with an amine of formula $R^9R^{10}NH$ wherein $R^9$ and $R^{10}$ are as defined above in an inert solvent e.g. ether or tetrahydrofuran at a temperature from 0° C. to the reflux temperature of the mixture.

According to a further feature of the present invention, compounds of formula (I) in which $R^2$ is —$CO_2H$, may be prepared by oxidising the corresponding compound of formula (I) in which $R^2$ is —CHO, which may be achieved by procedures reported in R. C. Larock in Comprehensive Organic Transformations p.838, e.g. by reaction with pyridinium dichromate in N,N-dimethylformamide at a temperature from 0 to 60° C.

According to a further feature of the present invention compounds of formula (I) in which $R^1$, $R^3$, $R^4$, $R^5$ and W are as defined above and $R^2$ represents a $C_1$ to $C_{10}$ alkyl group substituted by a group —$NR^9R^{10}$, may be prepared by the reaction of the corresponding compound of formula (I) in which the —$NR^9R^{10}$ group is replaced by a leaving group, preferably chlorine or bromine, with an amine of formula $R^9R^{10}NH$. The reaction is generally performed in an inert solvent e.g. ethanol at a temperature from 0 to 60° C.

According to a further feature of the present invention compounds of formula (I) in which $R^6$ is lower alkyl, alkenyl, alkenyl, —$COR^7$ or —$CO_2R^7$ may be prepared by reaction of the corresponding compound of formula (I) in which $R^6$ is hydrogen with a compound of formula $R^{61}$—$X^1$ wherein $R^{61}$ is lower alkyl, alkenyl, alkynyl, —$COR^7$ or —$CO_2R^7$ and $X^1$ is a leaving group. Preferably $X^1$ is halogen, especially chlorine. The reaction is generally performed in the presence of a base (e.g. sodium hydride) in an inert solvent (e.g. N,N-dimethylformamide) at a temperature from 0° C. to 60° C.

According to a further feature of the present invention compounds in which n is one or two are generally prepared by the oxidation of the sulphur atom of the corresponding compound in which n is zero or one. The oxidation of the sulphur atom is generally carried out using for example 3-chloroperbenzoic acid in an inert solvent such as dichloromethane at a temperature from –40° C. to room temperature.

Intermediates in the preparation of the compounds of the invention may be prepared by the application and adaptation of known methods, for example as described hereafter.

Acid chlorides of formula (II) may be prepared by the reaction of a compound of formula (IV) with a chlorinating agent, for example oxalyl chloride in an inert solvent such as dichloromethane or 1,2-dichloroethane optionally in the presence of a catalyst such as N,N-dimethylformamide at a temperature from –20° C. to the reflux temperature of the mixture.

Acid chlorides of formula (II) may also be prepared by the reaction of a carboxylic acid of formula IV above with a mixture of triphenylphosphine and carbon tetrachloride, for example as described in the published procedure of Lee in J. Am. Chem. Soc. (1966), 88, 3440.

Acids of formula (IV) may be prepared by the hydrolysis of an ester of formula (VI):

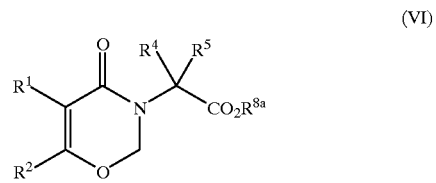

(VI)

wherein $R^1$, $R^2$, $R^4$ and $R^5$ are as defined above and $R^{8a}$ represents an alkyl group, preferably methyl or ethyl. The reaction is performed in the presence of a base for example sodium or potassium hydroxide and in a solvent, e.g. aqueous alcohol at a temperature from 0° C. to the reflux temperature of the solvent.

Acids of formula (IV) may also be prepared by the reaction of a benzyl ester of formula (VII):

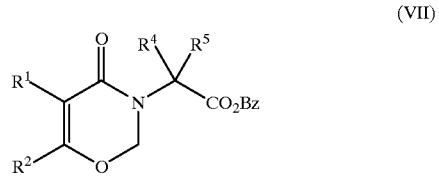

(VII)

wherein $R^1$, $R^2$, $R^4$ and $R^5$ are as defined above and Bz is benzyl, with aluminium bromide and anisole in the presence of nitromethane and in an inert solvent e.g. dichloromethane at a temperature from 0 to 50° C.

Tertiary butyl dimethylsilyl esters of formula (V) in which $R^1$, $R^2$, $R^4$, and $R^5$ are as defined above and TMS is replaced by a tert-butyldimethylsilyl group, may be prepared by the trans-esterification of a benzyl ester of formula (VII)-using tert butyldimethylsilane. The reaction is performed in the presence of a palladium catalyst e.g. Pd(OAc)$_2$ and a base e.g. triethylamine in an inert solvent e.g. dichloromethane at 0–60° C., according to the procedure described in Tetrahedron Letters (1986), vol. 27, pages 3753–3754.

Trimethylsilylesters of formula (V) may be prepared optionally in situ by reaction of a compound of formula (IV) above with chlorotrimethylsilane in an inert solvent, for example ether at 0° C. to the reflux temperature of the solvent.

Esters of formula (VI) or (VII) nay be prepared by the reaction of a compound of formula (VIII):

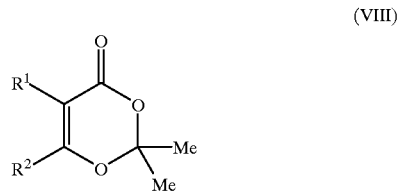

(VIII)

wherein $R^1$ and $R^2$ are as defined above, with an imine of formula $CH_2=NC(R^4)(R^5)CO_2R^{8a}$ or of formula $CH_2=NC(R^4)(R^5)CO_2Bz$ respectively, wherein $R^4$, $R^5$, $R^{8a}$ and Bz are as defined above. The reaction nay be performed in the presence or absence of a solvent and at a temperature from 90 to 200° C. or the boiling point of the solvent. When an inert solvent is used, for example xylene, the acetone produced is preferably removed by distillation.

Esters of formula (VI) or (VII) may also be prepared by the reaction of a compound of formula (IX):

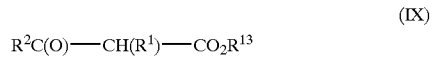

(IX)

wherein $R^1$ and $R^2$ are as defined above and $R^{13}$ represents an alkyl-group (preferably methyl or ethyl), with an imine of formula $CH_2=NC(R^4)(R^5)CO_2R^{8a}$ or $CH_2=NC(R^4)(R^5)CO2B_z$ respectively, wherein $R^4$, $R^5$, $R^{8a}$ and $B_z$ are as defined above. The reaction is performed utilising similar conditions to those used for the preparation of compounds of formula (VI) or (VII) from compounds of formula (VIII) above.

Imines of formula $CH_2=NC(R^4)(R^5)CO_2R^{8a}$ or of formula $CH_2=NC(R^4)(R^5)CO_2Bz$ may be prepared by the reaction of an aminoacid ester of formula $H_2N-C(R^4)(R^5)CO_2R^{8a}$ or of formula $H_2N-C(R^4)(R^5)CO_2Bz$ respectively, wherein $R^4$, $R^5$, $R^{8a}$ and Bz are as defined above, with formaldehyde, preferably as an aqueous solution and at a temperature from ambient to 60° C.

Intermediate compounds of formula (II), (IV), (V), (VI) and (VII) are novel and as such constitute a further feature of the present invention.

Compounds of formulae (III), (VIII) and (IX) are known or may be prepared using known methods, for example as described in International Patent Publication No. WO 93/15064.

The following non-limiting examples illustrate the invention.

EXAMPLE 1 m-Chloroperoxybenzoic acid (75% pure, 2.55 g) was added to a stirred solution of N-(2,5-difluorophenyl)-2-(2, 3-dihydro-6-methylthiomethyl-4-oxo-5-phenyl-4H-1,3-oxazin-3-yl)-2-methyipropanamide (1.00 g) in dichloromethane cooled in an ice/water bath. The mixture was stirred at ambient temperature for 2 hours, poured into saturated sodium bicarbonate solution and extracted with dichloromethane. The organic solution was washed in turn with saturated sodium bicarbonate solution and brine, dried (magnesium sulphate) and solvent evaporated under reduced pressure. The residue was purified by chromatography on silica gel, eluting with hexane/ethyl acetate to give N-(2,5-difluorophenyl)-2-(2,3-dihydro-6-methylsulphonylmethyl-4-oxo-5-phenyl-4H-1,3-oxazin-3-yl)-2-methyapropanamide (Compound 1, 0.21 g) a s a white solid, m.p. 160–162° C.

EXAMPLE 2

A solution of dicyclohexylcarbodiinide (10.04 g) in N,N-dimethyeformaeide was added to a stirred solution of 2-(2, 3-dihydro-6-methylthiomethyl-4-oxo-5-phenyl-4H-1,3-oxazin-3-yl)-2-methylpropanoic acid (13.00 g) in N,N-dimethylformamide at 20° C. 2,5-Difluoroaniline (7.84 g) was added to the solution at 20° C. and the solution was stirred at ambient temperature for 18 hours. The reaction mixture was diluted with ethyl acetate then added to water and the fine suspension removed by filtration. The organic layer was washed in turn with 0.5M hydrochloric acid, brine, 1.0M sodium carbonate and brine and then dried (magnesium sulphate). The organic solution was evaporated under reduced pressure and the residue was purified by chromatography on silica gel, eluting with dichioromethane to give N-(2,5-difluorophenyl)-2-(2,3-dihydro-6-methylthiomethyl-4-oxo-5-phenyl-4H-1,3-oxazin-3-yl)-2-methylpropanamide (Compound 3, 1.35 g) as a yellow solid, NMR (CDCl$_3$) 1.68(s,6H), 2.10(s,3H), 3.22(s,2H), 5.30(s, 2H), 6.64–6.76(m,1H), 6.95–7.05(m,1H), 7.25–7.38(m,5H), 8.11–8.21(m,2H).

By proceeding in a similar manner the following compound was also prepared: N-(3-trifluoromethylphenyl)-2-(2, 3-dihydro-6-methylthiomethyl-4-oxo-5-phenyl-4H-1,3-oxazin-3-yl)-2-methylpropanamide (compound 4) as an orange oil, NMR (CDCl$_3$) 1.72(s,6H), 2.10(s,3H), 3.23(s, 2H), 5.4(s,2H), 7.25–7.8(m,9H), 8.42(bs,1H).

EXAMPLE 3

To a stirred suspension of 2-(6-difluoromethyl-2,3-dihydro-4-oxo-5-phenyl-4H-1,3-oxazin-3-yl)-2-methylpropanoic acid (0.70g) in dichloromethane was added oxalylchloride (0.22 ml) followed by 1 drop of dimethylformamide. The reaction mixture was stirred at ambient temperature for 30 minutes and then cooled to 0° C. To the solution was added in turn triethylamine (0.36 ml), 3-aminobenzotrifluoride (0.34 g) and then triethylamine (0.36 ml). The reaction mixture was stirred at 0° C. for 30 minutes and at ambient temperature for 2 hours then washed in turn with water, 2M hydrochloric acid, water, 1M sodium carbonate and water. The organic solution was dried (magnesium sulphate) and evaporated under reduced pressure to give N-(3-trifluoromethylphenyl)-2-(6-difluoromethyl-2,3-dihydro-4-oxo-5-phenyl-4H-1,3-oxazin-3-yl)-2-methylpropanamide (compound 2, 0.25 g) as a beige solid, m.p. 58–60° C.

By proceeding in a similar manner the following compounds were prepared:

N-(3,5-dichlorophenyl)-2-(6-bromomethyl-2,3-dihydro-4-oxo-5-phenyl-4H-1,3-oxazin-3-yl)-2-methylpropanamide (compound 15) as a white solid, m.p. 122–125° C.;

N-(2,5-difluorophenyl)-2-(6-bromomethyl-2,3-dihydro-4-oxo-5-phenyl-4H-1,3-oxazin-3-yl)-2-methylpropanamide (compound 13), m.p. 125–127° C.;

N-(3,5-dichlorophenyl)-2-(2,3-dihydro-6-methoxymethyl-4-oxo-5-phenyl-4H-1,3-oxazin-3-yl)-2-methylpropanamide (compound 111) as a white solid, m.p. 120.5–122° C.;

N-(2,5-difluorophenyl)-2-(2,3-dihydro-6-methoxymethyl-4-oxo-5-phenyl-4H-1,3-oxazin-3-yl)-2-methylpropanamide (compound 35) as a yellow solid, m.p. 113–114.5° C.;

N-(3-trifluoromethylphenyl)-2-(2,3-dihydro-6-methoxymethyl-4-oxo-5-phenyl-4H-1,3-oxazin-3-yl)-2-methylpropanamide (compound 33) as a cream solid, m.p. 103–104.5° C.;

N-(3,5-dichlorophenyl)-2-(6-fluoromethyl-2,3-dihydro-4-oxo-5-phenyl-4H-1,3-oxazin-3-yl)-2-methylpropanamide (compound 112) as a yellow solid, m.p. 161–162.5° C.;

N-(2,5-difluorophenyl)-2-(6-fluoromethyl-2,3-dihydro-4-oxo-5-phenyl-4H-1,3-oxazin-3-yl)-2-methylpropanamide (compound 113) as a fawn solid, m.p. 140–141.5° C.;

N-(2,5-difluorophenyl)-2-(6-chloromethyl-2,3-dihydro-4-oxo-5-phenyl-4H-1,3-oxazin-3-yl)-2-methylpropanamide (compound 25) as a peach solid, m.p. 135.5–137° C.;

N-(3,5-dichlorophenyl)-2-(6-chloromethyl-2,3-dihydro-4-oxo-5-phenyl-4H-1,3-oxazin-3-yl)-2-methylpropanamide (compound 114) as a beige solid, m.p. 159–162° C.;

N-(3-trifluorophenyl)-2-(6-chloromethyl-2,3-dihydro-4-oxo-5-phenyl-4H-1,3-oxazin-3-yl)-2-methylpropanamide (compound 24) as an orange solid, m.p. 161.5–163° C.;

N-(5-chloro-2-methylphenyl)-2-(2,3-dihydro-6-methoxymethyl-4-oxo-5-phenyl-4H-I,3-oxazin-3-yl)-2-methylpropanamide (compound 124) as a cream solid, m.p. 116.5–117.5° C.;

N-(3-chlorophenyl)-2-(2,3-dihydro-6-methoxymethyl-4-oxo-5-phenyl-4H-1,3-oxazin-3-yl)-2-methylpropanamide (compound 34) as a yellow solid, m.p. 92.5–94.5° C.;

N-(2-fluoro-5-trifluoromethylphenyl)-2-(2,3-dihydro-6-methoxymethyl-4-oxo-5-phenyl-4H-1,3-oxazin-3-yl)-2-methylpropanamide (compound 36) as a white solid, m.p. 89–90.5° C.;

N-(2,5-difluorophenyl)-2-(6-ethoxymethyl-2,3-dihydro-4-oxo-5-phenyl-4H-1,3-oxazin-3-yl)-2-methylpropanamide (compound 125) as a yellow solid, m.p. 110–112.5° C.;

N-(3-trifluoromethylphenyl)-2-(6-ethoxymethyl-2,3-dihydro-4-oxo-5-phenyl-4H-1,3-oxazin-3-yl)-2-methylpropanamide (compound 37) m.p. 79.5–82° C.;

N-(3,5-dichlorophenyl)-2-(6-ethoxymethyl-2,3-dihydro-4-oxo-5-phenyl-4H-1,3-oxazin-3-yl)-2-methylpropanamide (compound 126) as a white solid, m.p. 129.5–131° C.;

N-(2-fluoro-5-trifluoromethylphenyl)-2-(6-fluoromethyl-2,3-dihydro-4-oxo-5-phenyl-4H-1,3-oxazin-3-yl)-2-methylpropanamide (compound 131) as a gum, NMR (CDCl$_3$)δ 1.66 (s,6H), 4.8(d,2H), 5.38(s,2H), 7.2–7.3 (m,8H);

N-(3,4,5-trifluorophenyl)-2-(6-fluoromethyl-2,3-dihydro-4-oxo-5-phenyl-4H-1,3-oxazin-3-yl)-2-methylpropanamide (compound 132), NMR(CDCl$_3$)δ 1.63(s,6H), 4.8(d,2H), 5.32(s,2H), 7.1–7.3(m,7H);

N-(3,5-difluorophenyl)-2-(6-fluoromethyl-2,3-dihydro-4-oxo-5-phenyl-4H-1,3-oxazin-3-yl)-2-methylpropanamide (compound 133), NMR (CDCl$_3$)δ 1.66(s,6H), 4.8(d,2H), 5.32(s,2H), 7.15–7.3(m,8H);

N-(2-chloro-3,5-difluorophenyl)-2-(6-fluoromethyl-2,3-dihydro-4-oxo-5-phenyl-4H-1,3-oxazin-3-yl)-2-methylpropanamide (compound 134), NMR (CDCl$_3$)δ 1.62(s,6H), 4.8(d,2H), 5.38(s,2H), 7.2–7.3(m,7H);

N-(3-trifluoromethylphenyl)-2-(6-fluoromethyl-2,3-dihydro-4-oxo-5-phenyl-4H-1,3-oxazin-3-yl)-2-methylpropanamide (compound 135), NMR (CDCl$_3$)δ 1.66(s,6H), 4.8(d,2H), 5.34(s,2H), 7.2–7.3(m,9H); and N-(3-chlorophenyl)-2-(6-fluoromethyl-2,3-dihydro-4-oxo-5-phenyl-4H-1,3-oxazin-3-yl)-2-methylpropanamide (compound 136), NMR (CDCl$_3$)δ 1.65(s,6H), 4.8(d,2H), 5.35(s,2H), 7.1–7.3(m,9H).

The following four compounds were prepared from 2-(6-cyclopropyl-2,3-dihydro-4-oxo-5-phenyl-4H-1,3-oxazin-3-yl)-2-methylpropanoic acid, and during the course of the reaction the cyclopropyl ring was opened with addition of the of HCl (produced in the course of the reaction) to generate the appropriate 6-(3-chloropropyl)substituted oxazinone derivatives:

N-(3,5-dichlorophenyl)-2-[6-(3-chloropropyl)-2,3-dihydro-4-oxo-5-phenyl-4H-1,3-oxazin-3-yl]-2-methylpropanamide (compound 137), m.p. 162.5–167° C.;

N-(3-chlorophenyl)-2-[6-(3-chloropropyl)-2,3-dihydro-4-oxo-5-phenyl-4H-1,3-oxazin-3-yl]-2-methylpropanamide (compound 138), m.p. 57–59° C.;

N-(3-trifluoromethylphenyl)-2-[6-(3-chloropropyl)-2,3-dihydro-4-oxo-5-phenyl-4H-1,3-oxazin-3-yl]-2-methylpropanamide (compound 139), m.p. 44–48.5° C.;

N-(2,5-difluorophenyl)-2-[6-(3-chloropropyl)-2,3-dihydro-4-oxo-5-phenyl-4H-1,3-oxazin-3-yl]-2-methylpropanamide (compound 140), m.p. 114.5–116° C.

EXAMPLE 4 m-Chloroperoxybenzoic acid (75% pure, 0.54 g) was added to a stirred solution of N-(2,5-difluorophenyl)-2-(2,3-dihydro-6-methylthiomethyl-4-oxo-5-phenyl-4H-1,3-oxazin-3-yl)-2-methylpropanamide (compound 1, 100 g) in dichloromethane at –20° C. The mixture was stirred at –20° C. for 1 hour, diluted with dichloromethane, washed with 1M sodium carbonate, dried (magnesium sulphate) and solvent evaporated under reduced pressure. The residue was triturated with diethyl ether to give N-(2,5-difluorophenyl)-2-(2,3-dihydro-6-methylsulphinylmethyl-4-oxo-5-phenyl-4H-1,3-oxazin-3-yl)-2-methylpropanamide (compound 5, 0.51 g) as a white solid, m.p. 124–128° C.

By proceeding in a similar manner the following compound was prepared:

N-(3-trifluoromethylphenyl)-2-(2,3-dihydro-6-methylsulphinylmethyl-4-oxo-5-phenyl-4H-1,3-oxazin-3-yl)-2-methyl-propananide (compound 6) as a white solid, m.p. 105–107° C.

EXAMPLE 5

A mixture of N-(3-chlorophenyl)-2-(6-bromomethyl-2,3-dihydro-4-oxo-5-phenyl-4H-1,3-oxazin-3-yl)-2- methylpropanamide (compound 8, 0.2 g) and sodium iodide (0.065 g) in acetone was heated under reflux for 18 hours, then evaporated to give a residue which was redissolved in ether. The ethereal solution was washed in turn with saturated aqueous sodium thiosulphate solution and water, dried (magnesium sulphate) and evaporated under reduced pressure to leave a residue which was purified by dry column chromatography on silica, eluting with ethyl acetate/dichloromethane to give N-(3-chlorophenyl)-2-(2,3-dihydro-6-iodomethyl-4-oxo-5-phenyl-4H-2,3-oxazin-3-yl)-2-methylpropanamide (compound 9, 0.04 g) as a white solid, m.p. 134.6–136.6° C.

EXAMPLE 6

A mixture of N-(3-chlorophenyl)-2-(2,3-dihydro-6-methyl-4-oxo-5-phenyl-4H-1,3-oxazin-3-yl)-2-methylpropanamide (1.0 g), N-bromosuccinimide (0.45 g), azobis-isobutyronitrile (10 mg) in carbon tetrachloride was heated at 65° C. for 2 hours. A second addition of N-bromosuccinimide (0.1 g) was made and the solution heated at 65° C. for a further 2 hours. The solution was then allowed to cool and the solvent removed under reduced pressure to give a brown residue, which was purified by dry column chromatography on silica, eluting with ethyl acetate/dichloromethane to give N-(3-chlorophenyl)-2-(6-bromomethyl-2,3-dihydro-4-oxo-5-phenyl-4H-1,3-oxazin-3-yl)-2-methylpropanamide (compound 8, 0.1 g) as a white solid, m.p. 89.8–90.8° C.

By proceeding in a similar manner, the following compounds were prepared:

N-(3-trifluoromethylphenyl)-2-(6-bromomethyl-2,3-dihydro-4-oxo-5-phenyl-4H-1,3-oxazin-3-yl)-2-methylpropanamide (compound 7), m.p. 159.8–161.2° C.;

and N-(3-chlorophenyl)-2-(6-dibromomethyl-2,3-dihydro-4-oxo-5-phenyl-4H-1,3-oxazin-3-yl)-2-methylpropanamide (compound 141), NMR (CDCl$_3$)δ 1.72(s,6H), 5.3(s,2H), 6.09(s,1H), 7.03–7.08(m,1H), 7.16–7.5(m,7H), 7.63(t,1H), 7.97(brs,1H).

EXAMPLE 7

N-(3,5-Dichlorophenyl)-2-(6-bromomethyl-2,3-dihydro-4-oxo-5-phenyl-4H-1,3-oxazin-3-yl)-2-methylpropanamide (compound 15, 1.0 g) was added to a stirred suspension of sodium thiomethoxide (0.18 g) in tetrahydrofuran. The mixture was stirred for 1 hour at room temperature, poured into a mixture of ether and water, and the ethereal layer washed with sodium hydroxide solution (0.5M) and with brine, dried (magnesium sulphate) and evaporated. The residue was purified by dry column chromatography on silica gel eluting with dichloromethane/iso-hexane then with iso-hexane/ethyl acetate to give N-(3,5-dichlorophenyl-2-(2,3-dihydro-6-methylthiomethyl-4-oxo-5-phenyl-4H-1,3-oxazin-3-yl)-2-methylpropanamide (compound 99, 0.63 g) as a white solid, m.p. 129–130° C.

By proceeding in a similar manner the following compounds were prepared:

N-(3,5-dichlorophenyl)-2-(6-ethylthiomethyl-2,3-dihydro-4-oxo-5-phenyl-4H-1,3-oxazin-3-yl)-2-methylpropanamide (compound 100) as a white solid, m.p. 104.5–105.5° C.; and N-(3-trifluoromethylphenyl)-2-(6-ethylthiomethyl-2,3-dihydro-4-oxo-5-phenyl-4H-1,3-oxazin-3-yl)-2-methylpropanamide (compound 101) as a white solid, m.p. 128–129° C.

EXAMPLE 8

A solution of potassium carbonate (0.33 g) in water was added portionwise to a stirred solution of N-(3-trifluoromethylphenyl)-2-(6-acetoxymethyl-2,3-dihydro-4-oxo-5-phenyl-4H-1,3-oxazin-3-yl)-2-methylpropanamide (0.8 g) in methanol. Stirring was continued for 4 hours at room temperature, the mixture evaporated and the residue dissolved in a mixture of ether and water. The organic layer was dried (magnesium sulphate), evaporated and the residue purified by dry column chromatography eluting with ether to give N-(3-trifluoromethylphenyl)-2-(2,3-dihydro-6-hydroxymethyl-4-oxo-5-phenyl-4H-1,3-oxazin-3-yl)-2-methylpropanamide (compound 102, 0.31 g) as a gum, NMR (CDCl$_3$)δ 1.7(s,6H), 4.1(d,2H), 5.3(s,2H), 7.1–7.3(m, 7H), 7.55(m,1H), 7.75(m,1H), 8.3(s,1H).

By proceeding in a similar manner the following compounds were prepared:

N-(3,5-dichlorophenyl)-2-(2,3-dihydro-6-hydroxymethyl-4-oxo-5-phenyl-4H-1,3-oxazin-3-yl)-2-methylpropanamide (compound 31), as an orange gum NMR (CDCl$_3$)δ 1.7(s,6H), 4.2(s,2H), 5.4(s,2H), 7.0(m,1H), 7.2–7.45(m,5H), 7.5(d,2H), 8.4(bs,$_1$H); and N-(2,5-difluorophenyl)-2-(2,3-dihydro-6-hydroxymethyl-4-oxo-5-phenyl-4H-1, 3-oxazin-3-yl)-2-methylpropanamide (compound 130) as a yellow solid, m.p. 69.5–71.5° C. This compound was also used in the preparation of compound 129 (see Example 18).

EXAMPLE 9

A mixture of N-(3-trifluoromethylphenyl)-2-(6-bromomethyl-2,3-dihydro-4-oxo-5-phenyl-4H-1,3-oxazin-3-yl)-2-methylpropanamide (1.09 g) and sodium acetate (0.36 g) was heated at 80–90° C. in N,N-dimethylformamide for 3 hours. The cooled solution was diluted with ether, washed with water, dried (magnesium sulphate) and evaporated in vacuo to give N-(3-trifluoromethylphenyl)-2-(6-acetoxymethyl-2,3-dihydro-4-oxo-5-phenyl-4H-1,3-oxazin-3-yl)-2-methylpropanamide (compound 103, 0.81 g) as a white solid, m.p. 76.5–77.5° C.

By proceeding in a similar manner the following compound was prepared:

N-(3,5-dichlorophenyl)-2-(6-acetoxymethyl-2,3-dihydro-4-oxo-5-phenyl-4H-1,3-oxazin-3-yl)-2-methyipropanamide (compound 104) as a yellow solid, m.p. 125–126° C.

EXAMPLE 10

Methylamine (2 ml of a 33% solution in ethanol) was added to a stirred suspension of N-(3-trifluoromethylphenyl)-2-(6-bromomethyl-2,3-dihydro-4-oxo-5-phenyl-4H-1,3-oxazin-3-yl)-2-methylpropanamide (0.5 g) in ethanol. Stirring was maintained at room temperature for 1 hour. The solution was diluted (ethyl acetate), washed (water), dried (magnesium sulphate) and evaporated. The residue was purified by dry column chromatography on silica gel, eluting with methanol/hexane to give N-(3-trifluoromethylphenyl)-2-(2,3-dihydro-6-methylaminomethyl-4-oxo-5-phenyl-4H-1,3-oxazin-3-yl)-2-methylpropanamide (compound 105, 0.21 g) as an orange gum, NMR (CDCl$_3$)δ 1.6(s,6H), 2.25(s,3H), 3.25(s,2H), 5.3(s,2H), 7.1–7.3(m,8H), 7.55(m,1H), 7.75(s,1H), 8.45(s, 1H);

By proceeding in a similar manner the following compounds were prepared:

N-(3-trifluoromethylphenyl)-2-(2,3-dihydro-6-dimethylaminomethyl-4-oxo-5-phenyl-4H-1,3-oxazin- 3-yl)-2-methylpropanamide (compound 106) as a brown gum, NMR (CDCl$_3$)δ 1.6(s,6H), 2.12(s,6H), 3.0(s,2H), 5.3(s,2H), 7.0–7.3(m,7H), 7.55(m,1H), 7.7 (m,1H), 8.4(m,1H);

N-(3,5-dichlorophenyl)-2-(2,3-dihydro-6-dimethylaminomethyl-4-oxo-5-phenyl-4H-1,3-oxazin-3-yl)-2-methylpropanamide (compound 107), m.p. 75–76° C.; and N-(3,5-dichlorophenyl)-2-(2,3-dihydro-6-methylaminomethyl-4-oxo-5-phenyl-4H-1,3-oxazin-3-yl)-2-methylpropanamide (compound 108) as a cream solid, m.p. 60–66° C.

EXAMPLE 11

A solution of N-(3,5-dichlorophenyl)-2-(2,3-dihydro-6-hydroxymethyl-4-oxo-5-phenyl-4H-1,3-oxazin-3-yl)-2-methylpropanamide (0.6 g) in dichloromethane was added to a suspension of pyridinium chlorochromate (0.45 g) in dichloromethane stirred at room temperature. After 1.5 hours, the mixture was diluted with ethyl acetate, washed (water), dried (magnesium sulphate) and evaporated. The residue was purified by dry column chromatography on silica gel, eluting with ethyl acetate to give N-(3,5-dichliorophenyl)-2-(2,3-dihydro-6-formyl-4-oxo-5-phenyl-4H-1,3-oxazin-3-yl)-2-methylpropanamide (compound 109, 0.35 g) as a yellow solid, m.p. 144–146° C.

By proceeding in a similar manner but starting from N-(3,5-dichlorophenyl)-2[2,3-dihydro-6-(1-hydroxyethyl)-4-oxo-5-phenyl-4H-1,3-oxazin-3-yl]-2-methylpropanamide and in the additional presence of powdered 4A molecular sieve N-(3,5-dichlorophenyl)-2-(6-acetyl-2,3-dihydro-4-oxo-5-phenyl-4H-1,3-oxazin-3-yl)- 2-methylpropanamide (compound 127) was prepared as a yellow solid, m.p. 92–95° C.

EXAMPLE 12

Oxalyl chloride (0.2 ml) followed by N,N-dimethylformamide (1 drop), was added to a solution of tert butyl dimethylsilyl 2-(6-acetoxymethyl-2,3-dihydro-4-oxo-5-phenyl-4H-1,3-oxazin-3-yl)-2-methylpropanoate (0.92 g) in dichloromethane. The mixture was stirred for 0.5 hours, and a solution of 2,5-difluoroaniline (0.3 g) in dichloromethane added. After 0.3 hours triethylamine (0.6 ml) was added, the solution stirred for 1 hour, and then evaporated. The residue was dissolved in ethyl acetate, washed with water, hydrochloric acid (2M) and with sodium bicarbonate solution, dried (magnesium sulphate) and evaporated. The residue was purified by dry column chromatography on silica gel, eluting with ethyl acetate to give N-(2,5-difluorophenyl)-2-(6-acetoxymethyl-2,3-dihydro-4-oxo-5-phenyl-4H-1,3-oxazin-3-yl)-2-methylpropanamide (compound 110, 0.18 g) as a gum, N (CDCl$_3$)δ 1.5(s,6H), 2.1(s,3H), 4.6(s,2H), 5.4(s,2H), 6.65(m,1H), 6.95(m,1H), 7.2–7.4(m,5H), 8.05(s,1H), 8.1(m,1H).

By proceeding in a similar manner N-(2-chloro-5-methylphenyl)-2-(2,3-dihydro-6-methoxymethyl-4-oxo-5-phenyl-4H-1,3-oxazin-3-yl)-2-methylpropanamide (compound 122) was prepared as an orange solid, m.p. 87–90° C.

EXAMPLE 13

Hydroxylamine hydrochloride (0.31 g) followed by sodium acetate (0.37 g) was added to a stirred solution of N-(3,5-dichlorophenyl)-2-( 6-formyl-2,3-dihydro-4-oxo-5-phenyl-4H-1,3-oxazin-3-yl)-2-methylpropanamide (1.5 g) in ethanol at room temperature. After 10 minutes the precipitated solid was filtered, washed with ethanol and water, and dried to give N-(3,5-dichlorophenyl)-2-(2,3-dihydro-6-hydroxyiminomethylene-4-oxo-5-phenyl-4H-1,3-oxazin-3-yl)-2-methylpropanamide (compound 115, 0.53 g) m.p. 207.5–209.5° C.

By proceeding in a similar manner but employing the appropriate O-alkylhydroxylamine derivative the following compounds were prepared:

N-(3,5-dichlorophenyl)-2-(6-ethoxyiminomethylene-2,3-dihydro-4-oxo-5-phenyl-4H-1,3-oxazin-3-yl)-2-methylpropanamide (compound 116) as a cream solid, m.p. 184.5–186.5° C.;

N-(3,5-dichlorophenyl)-2-(2,3-dihydro-6-methoxyiminomethylene-4-oxo-5-phenyl-4H-1,3-oxazin-3-yl)-2-methylpropanamide (compound 117) as a pale yellow solid, m.p. 179–181.5° C.; and N-(2,5-difluorophenyl)-2-(2,3-dihydro-6-methoxyiminomethylene-4-oxo-5-phenyl-4H-1,3-oxazin-3-yl)-2-methylpropanamide (compound 128) as a white solid, m.p. 189.5–190.5° C.

EXAMPLE 14

Acetic anhydride (3 ml) was added to a stirred solution of N-(3,5-dichlorophenyl)-2-(2,3-dihydro-6-hydroxyiminomethylene-4-oxo-5-phenyl-4H-1,3-oxazin-3-yl)-2-methylpropanamide (0.4 g) in pyridine (3 ml) at −5° C. After 1.5 hours the mixture was poured into ice/water and extracted (ethyl acetate). The extract was washed with hydrochloric acid (2M) and with brine, dried (magnesium sulphate) and evaporated. The residue was purified by dry column chromatography on silica gel, eluting with hexane/ethyl acetate to give N-(3,5-dichlorophenyl)-2-(6-acetoxyiminomethylene-2,3-dihydro-4-oxo-5-phenyl-4H-1,3-oxazin-3-yl)-2-methylpropanamide (compound 118, 0.32 g) as an off-white solid, m.p. 125–127° C.

EXAMPLE 15

Hydrazine hydrate (0.06 ml) was added to a stirred solution of N-(3,5-dichlorophenyl)-2-(2,3-dihydro-6-formyl-4-oxo-5-phenyl-4H-1,3-oxazine-3-yl)-2-methylpropanamide (0.5 g) in ethanol at room temperature. After 0.5 hours the solvent was evaporated, the residue dissolved in ethyl acetate and washed with water and brine, dried (magnesium sulphate) and evaporated. The residue was purified by dry column chromatography on silica gel, eluting with hexane/ethyl acetate to give N-(3,5-dichlorophenyl)-2-(6-aminoiminomethylene-2,3-dihydro-4-oxo-5-phenyl-4H-1,3-oxazin-3-yl)-2-methylpropanamide (compound 119, 0.19 g) as a pale yellow solid, m.p. 153–155° C.

By proceeding in a similar manner N-(3,5-dichlorophenyl)-2-(2,3-dihydro-6-methylaminoiminomethylene-4-oxo-5-phenyl-4H-1,3-oxazin-3-yl)-2-methylpropanamide (compound 121) was prepared as a beige solid, m.p. 146–149° C.

EXAMPLE 16

Trifluoroacetic anhydride (3 ml) was added to a stirred solution of N-(3,5-dichlorophenyl)-2-(2,3-dihydro-6-hydroxyiminomethylene-4-oxo-5-phenyl-4H-2,3-oxazin-3-yl)-2-methylpropanamide (0.4 g) in pyridine (4 ml) at −5° C. After 0.5 hours ice and ethyl acetate was added and the mixture stirred for 1 hour. The organic phase was washed (water), dried (magnesium sulphate) and evaporated. The residue was purified by dry column chromatography on silica gel, eluting with hexane/ethyl acetate to give N-(3,5-dichlorophenyl)-2-(6-cyano-2,3-dihydro-4-oxo-5-phenyl-4H-1,3-oxazin-3-yl)-2-methylpropanamide (compound 120, 0.16 g) as a white solid, m.p. 132.5–135° C.

EXAMPLE 17

Methylmagnesium bromide (1.7 ml of a 3M solution in ether) was added dropwise to a stirred solution of N-(3,5-dichlorophenyl)-2-(6-formyl-2,3-dihydro-4-oxo-5-phenyl-4H-1,3-oxazin-3-yl)-2-methylpropanamide (1.0 g) in dry tetrahydrofuran under an inert atmosphere at –5° C. After 1 hour at that temperature, ammonium chloride solution (saturated) and ethyl acetate were added. The organic phase was washed (brine), dried (magnesium sulphate) and evaporated. The residue was purified by dry column chromatography on silica gel, eluting with dichloromethane/ethyl acetate to give N-(3,5-dichlorophenyl)-2[2,3-dihydro-6-(1-hydroxyethyl)-4-oxo-5-phenyl-4H-1,3-oxazin-3-yl]-2-methylpropanamide (compound 123, 0.27 g) as a cream solid, m.p. 85–88° C.

EXAMPLE 18

A solution of N-(2,5-difluorophenyl)-2-(2,3-dihydro-6-hydroxymethyl-4-oxo-5-phenyl-4H-1,3-oxazin-3-yl)-2-methylpropanamide (1.0 g) in dichloromethane was added to a stirred mixture of pyridinium chlorochromate (0.8 g) and powdered 4A molecular sieve (1.6 g) in dichloromethene. After 2 hours the mixture was purified directly by dry column chromatography on silica gel, eluting with dichloromethane to give N-(2,5-difluorophenyl)-2-(2,3-dihydro-6-formyl-4-oxo-5-phenyl-4H-1,3-oxazin-3-yl)-2-methylpropanamide (compound 129, 0.83 g) as a pale green solid, m.p. 76–77.5° C.

REFERENCE EXAMPLE 1

A solution of sodium hydroxide (16.43 g) in 10 water was added to a stirred solution of ethyl 2-(2,3-dihydro-6-methylthiomethyl-4-oxo-5-phenyl-4H-1,3-oxazin-3-yl)-2-methylpropanoate (68 g) in a mixture of ethanol and 1,4-dioxan. The solution was heated at 60° C. for 6 hours, allowed to cool and the solvent was removed under reduced pressure to give an orange oil which was dissolved in water. The aqueous solution was washed with dichloromethane, acidified to pH 1 with concentrated hydrochloric acid, extracted with dichloromethane, the extract dried (magnesium sulphate) and evaporated under reduced pressure. The residue was purified by chromatography on silica gel, eluting with dichloromethane/ethyl acetate to give 2-(2,3-dihydro-6-methylthiomethyl-4-oxo-5-phenyl-4H-1,3-oxazin-3-yl)-2-methylpropanoic acid (24.2 g) as a yellow solid, m.p. 136–137° C.

By proceeding in a similar manner the following compounds were prepared:

2-(2,3-dihydro-6-methyl-4-cxo-5-phenyl-4H-1,3-oxazin-3-yl)-2-methylpropanoic acid as a white solid, m.p. 200.5–201.5° C.; and 2-(6-cyclopropyl-2,3-dihydro-4-oxo-5-phenyl-4H-1,3-oxazin-3-yl)-2-methylpropanoic acid, m.p. 138.5–189.5° C.

REFERENCE EXAMPLE 2

A solution of 2,2-dimethyl-6-methylthiomethyl-6-phenyl-4H-1,3-dioxin-4-one (51.64 g) and ethyl 2-(N-methyleneamino)-2-methylpropanoate (30.98 g) in xylene was heated in an oil bath for 2 hours, the oil bath temperature being maintained at 180° C. During the reaction the acetone produced was removed by distillation and an equal volume of xylene was added to keep the concentration the same. The solution was allowed to cool and evaporated under reduced pressure to give ethyl 2-(2,3-dihydro-6-methylthiomethyl-4-oxo-5-phenyl-4H-2,3-oxazin-3-yl)-2-methylpropanoate as an orange oil (68 g), NNR (CDCl$_3$) 1.23(t,3H), 1.56(s,6H), 2.09(s,3H), 3.22(s,2H), 4.16(q,2H), 5.35(s,2H), 7.25–7.4 (m,5H).

By proceeding in a similar manner the following compounds were prepared:

benzyl 2-(6-acetoxymethyl-2,3-dihydro-4-oxo-5-phenyl-4H-2,3-oxazin-3-yl)-2-methylpropanoate as a white solid (2.7 g), m.p. 105–106° C.;

ethyl 2-(2,3-dihydro-6-methyl-4-oxo-5-phenyl-4H-2,3-oxazin-3-yl)-2-methylpropanoate as an orange oil, NMR (CDCl$_3$), 1.22(t,3H), 1.58(s,6H), 2.90(s,3H), 4.12(q,2H), 5.28(s,2H), 7.2–7.48(m,5H); and tert butyl 2-(6-acetoxymethyl-2,3-dihydro-4-oxo-5-phenyl-4H-2,3-oxazin-3-yl)-2-methylpropanoate, as a yellow solid, m.p. 125–125.7° C.

REFERENCE EXAMPLE 3

Sodium thiomethoxide (39.75 g) was added in portions to a stirred solution of 6-bromomethyl-2,2-dimethyl-5-phemyl-4H-2,3-dioxin-4-one (168.8 g) in N,N-dimethylformamide at 10° C. After stirring at ambient temperature for 18 hours the solution was poured into water and extracted with ethyl acetate. The organic solution was washed in turn with water and brine and dried (magnesium sulphate). The organic solution was evaporated under reduced pressure and the residue purified by chromatography on silica gel, eluting with hexane/dichloromethane, to give 2,2-dimethyl-6-methylthiomethyl-5-phenyl-4H-1,3-dioxin-4-one (103.3 g) as a yellow solid, NMR (CDCl$_3$) 1.80(s,6H), 2.12(s,3H), 3.20(s,2H), 7.26–7.41(m,5H).

REFERENCE EXAMPLE 4

A stirred suspension of 2-amino-2-methylpropanoic acid (165 g) in ethanol at 0° C. was saturated with hydrogen chloride gas. The mixture was heated at reflux for 4 hours and the solvent was evaporated under reduced pressure to give ethyl 2-amino-2-methylpropanoate hydrochloride as a white solid. Sodium carbonate (100 g) was slowly added to a suspension of the solid in water followed by 40% aqueous formaldehyde solution (150 g) and the suspension was stirred for 3 hours. The mixture was extracted with ether, the organic solution was washed with water, dried (magnesium sulphate) and solvent evaporated under reduced pressure to give ethyl 2-(N-methyleneamino)-2-methylpropanoate (137.8 g) in equilibrium with its trimer 1,3,5-tri(1-ethoxycarbonyl-1-methylethyl)hexahydrotriazine as a colourless oil, IR (liquid film) 2980(s), 1725(vs), 1250(s), 1140(vs).

By proceeding in a similar manner the following compound was prepared:

tert butyl 2-(N-methyleneamino)-2-methylpropanoate as a yellow liquid, IR (liquid film) 2978(m), 1725(s), 1370(m), 1250(m), 1135(vs) cm$^{-1}$.

REFERENCE EXAMPLE 5

A solution of aluminium tribromide (3.85 g) in nitromethane was added in portions to a stirred solution of benzyl 2-(6-difluoromethyl-2,3-dihydro-4-oxo-5-phenyl- 4H-1,3-oxazin-3-yl)-2-methylpropanoate (1.93 g) and anisole (3.1 g) in dichloromethane at 0° C. under an inert atmosphere. The reaction mixture was stirred at 0° C. for 10 minutes and at ambient temperature for 2 hours and diluted with dichloromethane. The dichloromethane solution was washed in turn with 2 M hydrochloric acid and with water. The organic solution was extracted with 1 M sodium bicarbonate, the aqueous extract was then washed with diethyl ether and acidified to pH 1 with 2 M hydrochloric acid. The acidic solution was extracted with ethyl acetate, the extract was dried (magnesium sulphate) and evaporated under reduced pressure to give 2-(6-difluoromethyl-2,3-dihydro-4-oxo-5-phenyl-4H-1, 3-oxazin-3-yl)-2-methylpropanoic acid (0.70 g) as a pink solid, m.p. 149–151° C.

By proceeding in a similar manner the following compound was prepared:

2-(6-bromomethyl-2,3-dihydro-4-oxo-5-phenyl-4H-1,3-oxazin-3-yl)-2-methylpropanoic acid as a yellow solid, NMR (CDCl$_3$) 1.55(s,6H), 3.8(s,2H), 5.3(s,2H), 7.3(m, 5H).

REFERENCE EXAMPLE 6

Diethylaminosulphur trifluoride (1.3 ml) was added to a stirred solution of benzyl 2-(6-formyl-2,3-dihydro-4-oxo-5-phenyl-4H-1,3-oxazin-3-yl)-2-methylpropanoate (2.0 g) in dichloromethane at 0° C. The solution was stirred at 0° C. for 0.5 hours and at ambient temperature for 3 hours. The solution was poured into saturated aqueous ammonium chloride, the organic phase was dried (magnesium sulphate) and evaporated under reduced pressure to give benzyl 2-(6-difluoromethyl-2,3-dihydro-4-oxo-5-phenyl-4H-1,3-oxazin-3-yl)-2-methylpropanoate (2.1 g) as a yellow gum, MM (CDCl$_3$) 1.55(s,6H), 4.95(s,2H), 5.2(s,2H), 5.95(t,1H), 7.15–7.4 (m,10H).

REFERENCE EXAMPLE 7

A solution of benzyl 2-(2,3-dihydro-6-hydroxymethyl-4-oxo-5-phenyl-4H-1,3-oxazin-3-yl)-2-methylpropanoate (2.0 g) in dichloromethane was added over 5 minutes to a stirred suspension of pyridinium chlorochromate (0.9 g) in dichloromethane at ambient temperature. After stirring for 1 hour the reaction mixture was diluted with dichloromethane and washed with water. The organic solution was dried (magnesium sulphate) and solvent evaporated under reduced pressure to give benzyl 2-(6-formyl-2,3-dihydro-4-oxo-5-phenyl-4H-1,3-oxazin-3-yl)-2-methylpropanoate (0.85 g) as an orange gum, NMR (CDCl$_3$) 1.5(s,6H), 5.1(s,2H), 5.3(s, 2H), 7.2(bs,5H), 7.3–7.4(m,5H), 9.25(s,1H).

REFERENCE EXAMPLE 8

A solution of potassium carbonate (0.96 g) in water was added in portions to a stirred solution of benzyl 2-(6-acetoxymethyl-2,3-dihydro-4-oxo-5-phenyl-4H-1,3-oxazin-3-yl)-2-methylpropanoate (2.70 g) in methanol at 0° C. The mixture was stirred at ambient temperature for 1 hour and the solvent was evaporated under reduced pressure. The residue was acidified with 2 M hydrochloric acid, extracted with diethyl ether, the extract was dried (magnesium sulphate) and the solvent evaporated under reduced pressure to give benzyl 2-(2,3-dihydro-6-hydroxymethyl-4-oxo-5-phenyl-4H-1,3-oxazin-3-yl)-2-methylpropanoate (2.51 g) as a yellow gum, NMR (CDCl$_3$) 1.6(s,6H), 4.15(s,2H), 5.1(s, 2H), 5.3(s,2H), 7.26–7.42(m,10H).

By proceeding in a similar manner the following compound was prepared:

tert butyl 2-(2,3-dihydro-6-hydroxymethyl-4-oxo-5-phenyl-4H-1,3-oxazin-3-yl)-2-methylpropanoate as a cream solid, m.p. 115–116.5° C.

REFERENCE EXAMPLE 9

37% Aqueous formaldehyde solution (17.3 g) was added over 10 minutes to a stirred solution of benzyl 2-amino-2-methylpropanoate (28.0 g) in diethyl ether at ambient temperature. The two phase mixture was stirred for 2½ hours then diluted with diethyl ether and washed with brine. The ethereal solution was dried (magnesium sulphate) and solvent evaporated under reduced pressure to give benzyl 2-(N-methyleneamino)-2-methylpropanoate (29.4 g) in equilibrium with its trimer 1,3,5-tri(1-benzyloxycarbonyl-1-methylethyl)hexahydrotriazine as a colourless oil, IR (liquid film) 2980(m), 1725(vs), 1250(m), 1135(vs).

REFERENCE EXAMPLE 10

A mixture of 2-(2,3-dihydro-6-methyl-4-oxo-5-phenyl-4H-1,3-oxazin-3-yl)-2-methylpropanoic acid (27.5 g) and triphenylphosphine (34.5 g) in tetrachloromethane (173 ml) and dichloromethane was heated at reflux for 45 minutes. The reaction mixture was cooled in an ice bath and 3-chloroaniline (12.8 g) and then triethylamine (14.0 ml) were added dropwise with stirring. The mixture was stirred at ambient temperature for 2 hours and evaporated under reduced pressure. The residue was suspended in ethyl acetate and the insoluble material removed by filtration. The filtrate was evaporated under reduced pressure and the residue purified by chromatography on silica gel, eluting with ethyl acetate/hexane to give N-(3-chlorophenyl)-2-(2, 3-dihydro-6-methyl-4-oxo-5-phenyl-4H-1,3-oxazin-3-yl)-2-methylpropanamide (28.8 g) as a white solid, m.p. 146.5–149.9° C.

By proceeding in a similar manner N-(3-trifluoromethylphenyl)-2-methyl-2-(6-methyl-5-phenyl-2, 3-dihydro-4-oxo-4H-1,3-oxazin-3-yl)propanamide was prepared, m.p. 113.5–114.5° C.

REFERENCE EXAMPLE 11

By following the procedure described in Example 3, there was prepared the following intermediate:

N-(3-trifluoromethylphenyl)-2-(2,3-dihydro-6-methyl-4-oxo-5-phenyl-4H-1,3-oxazin-3-yl)-2-methylpropanamide, as a white solid, m.p. 140.8–141.6° C.

REFERENCE EXAMPLE 12

A solution of phosphorus tribromide (5.1 ml) in ether was added during 0.5 hour to a solution of benzyl 2-(2,3-dihydro-6-hydroxymethyl-4-oxo-5-phenyl-4H-1,3-oxazin-3-yl)-2-methylpropanoate (61.1 g) in a mixture of ether and tetrahydrofuran at −78° C. The mixture was then stirred at −10° C. for 4 hours and at room temperature for 1 hour, then washed (water), dried (magnesium sulphate) and evaporated. Purification of the residue by dry column chromatography on silica gel gave benzyl 2-(6-bromomethyl-2,3-dihydro-4-oxo-5-phenyl-4H-1,3-oxazin-3-yl)-2-methylpropanoate (46.1 g), NMR(CDCl$_3$) 1.5(s,6H), 3.8(s, 2H), 5.05(s,2H), 5.3(s,2H), 7.2(s,5H).

REFERENCE EXAMPLE 13

A mixture of palladium (II) acetate (25 mg), tert butyl-dimethylsilane (1.25 ml) and triethylamine (0.05 ml) in dichloromethane was stirred at room temperature under an inert atmosphere for 0.25 hour. A solution of benzyl 2-(6-acetoxymethyl-2,3-dihydro-4-oxo-5-phenyl-4H-1,3-oxazin-3-yl)-2-methylpropanoate (1.0 g) was added and stirring continued for 18 hours. The mixture was filtered (hyflo) and evaporated to give tert butyldimethylsilyl 2-(6-acetoxymethyl-2,3-dihydro-4-oxo-5-phenyl-4H-1,3-oxazin-3-yl)-2-methylpropanoate (0.92 g) as a yellow oil, NMR (CDCl$_3$)δ 0.25(s,9H), 1.5(s,6H), 2.0(s,3H), 4.5(s,2H), 5.2(s, 2H), 7.0–7.3(m,5H).

By proceeding in a similar manner the following compounds were prepared:

tert butyl dimethylsilyl 2-(2,3-dihydro-6-methoxymethyl-4-oxo-5-phenyl-4H-1,3-oxazin-3-yl)-2-methylpropanoate as a yellow oil, NMR (CDCl$_3$)δ 0.15(s,6H), 0.79(s,9H), 1.43(s,6H), 3.22(s,3H), 3.83(s, 2H), 5.22(s,2H), 7.1–7.3(m,5H); and tert butyl dimethylsilyl 2-(6-ethoxymethyl-2,3-dihydro-4-oxo-5-phenyl-4H-1,3-oxazin-3-yl)-2-methylpropanoate as a pale yellow oil, used directly in the next stage since it was not very stable.

REFERENCE EXAMPLE 14

A mixture of tert butyl 2-(2,3-dihydro-6-methoxymethyl-4-oxo-5-phenyl-4H-1,3-oxazin-3-yl)-2-methylpropanoate (2.6 g) and trifluoroacetic acid (2.05 g) was stirred in dichloromethane for 20 hours at 35° C. A further addition of trifluoroacetic acid (0.82 g) was made and the solution heated under reflux for 24 hours. The cooled mixture was diluted (dichloromethane) and extracted (sodium carbonate solution). The aqueous extract was acidified (2 M hydrochloric acid solution), extracted (ethyl acetate), dried (magnesium sulphate) and evaporated. The residue was dissolved in ethyl acetate and evaporated (three times) redissolved in hexane and evaporated to give 2-(2,3-dihydro-6-methoxymethyl-4-oxo-5-phenyl-4H-1,3-oxazin-3-yl)-2-methylpropanoic acid (1.74 g) as a white solid, m.p. 135–138° C.

By proceeding in a similar manner the following compounds were prepared:

2-(6-fluoromethyl-2,3-dihydro-4-oxo-5-phenyl-4H-1,3-oxazin-3-yl)-2-methylpropanoic acid, m.p. 176–177.5° C. (dec); and 2-(6-chloromethyl-2,3-dihydro-4-oxo-5-phenyl-4H-1,3-oxazin-3-yl)-2-methylpropanoic acid as a cream solid, m.p. 157.5–158.5° (dec).

REFERENCE EXAMPLE 15

A mixture of tert butyl 2-(2,3-dihydro-6-hydroxyethyl-4-oxo-5-phenyl-4H-1,3-oxazin-3-yl)-2-methylpropanoate (4.0 g), methyl iodide (32.7 g) and silver(I)oxide (4.27 g, freshly prepared) was stirred and heated in dry acetonitrile under reflux for 16 hours. A further addition of methyl iodide (7.1 g) and silver(I)oxide (1.19 g) was made, and heating continued for 5 hours. The mixture was cooled, filtered and evaporated. The residue was purified by dry column chromatography on silica gel, eluting with hexane to give tert butyl 2-(2,3-dihydro-6-methoxymethyl-4-oxo-5-phenyl-4H-1,3-oxazin-3-yl)-2-methylpropanoate (2.95 g) as a white solid, m.p. 106–106.8° C.

By proceeding in a similar manner the following compounds were prepared:

benzyl 2-(2,3-dihydro-6-methoxymethyl-4-oxo-5-phenyl-4H-1,3-oxazin-3-yl)-2-methylpropancate as a yellow oil, NMR (CDCl$_3$)δ 1.53(s,6H), 3.22(s,3H), 3.85(s,2H), 5.05(s,2H), 5.23(s,2H), 7.15–7.25(m,10H);

benzyl 2-(6-ethoxymethyl-2,3-dihydro-4-oxo-5-phenyl-4H-1,3-oxazin-3-yl)-2-methylpropanoate as a yellow solid, m.p. 65–67° C.

REFERENCE EXAMPLE 16

Diethylaminosulphur trifluoride (1.27 ml) was added to a stirred solution of tert butyl 2-(2,3-dihydro-6-hydroxymethyl-4-oxo-5-phenyl-4H-1,3-oxazin-3-yl)-2-methylpropanoate (3.5 g) in dichloromethane at −78° C. After 0.5 hour the solution was allowed to warm to room temperature and stirred for 16 hours. The mixture was poured into saturated ammonium chloride solution and the organic phase washed (brine), dried (magnesium sulphate) and evaporated. The residue was purified by dry column chromatography on silica get, eluting with dichloromethane/hexane (1:1) to give tert butyl 2-(6-fluoromethyl-2,3-dihydro-4-oxo-5-phenyl- 4H-1,3-oxazin-3-yl)-2-methylpropanoate (1.31 g) as a white solid, m.p. 80.5–82.5° C.

REFERENCE EXAMPLE 17

A solution of triphenylphosphine (1.82 g) in tetrahydrofuran was added dropwise to a stirred solution of N-chlorosuccinimide (1.08 g) in tetrahydrofuran. After 10 minutes a solution of tert butyl 2-(2,3-dihydro-6-hydroxymethyl-4-oxo-5-phenyl-4H-1,3-oxazin-3-yl)-2-methylpropanoate (2.0 g) in tetrahydrofuran was added. The mixture was stirred overnight and partitioned between ether and water, and the organic phase washed (brine), dried (magnesium sulphate) and evaporated. The residue was purified by dry column chromatography on silica gel, eluting with dichloromethanelhexane (2:1) to give tert butyl 2-(6-chloromethyl-2,3-dihydro-4-oxo-5-phenyl-4H-1,3-oxazin-3-yl)-2-methylpropanoate (1.49 g) as a white solid, m.p. 128–129° C.

REFERENCE EXAMPLE 18

A solution of potassium carbonate (0.57 g) in water was added to a stirred solution of tert butyl dimethylsilyl 2-(6-ethoxymethyl-2,3-dihydro-4-oxo-5-phenyl-4H-1,3-oxazin-3-yl)-2-methylpropanoate (2.1 g) in a mixture of tetrahydrofuran and methanol (1:1) at room temperature. After 1 hour, hydrochloric acid (2 M) was added until neutral, and the ethanol evaporated. The residue was distributed between ethyl acetate and hydrochloric acid (2 M), and the organic phase washed (brine), dried (magnesium sulphate) and evaporated to give 2-(6-etboxymethyl-2,3-dihydro-4-oxo-5-phenyl-4H-1,3-oxazin-3-yl)-2-methylpropanoic acid (1.35 g) as a white solid, m.p. 160–161° C.

REFERENCE EXAMPLE 19

A mixture of methyl 3-cyclopropyl-3-oxo-2-phenylpropanoate (6.54 g) and ethyl 2-(N-methyleneamino)-2-methylpropanoate was heated under reflux in xylene in the presence of 5A molecular sieve (33 g) for 7 hours. The mixture was evaporated and purified by chromatography on silica gel, eluting with hexane/ethyl acetate (7:3) to give ethyl 2-(6-cyclopropyl-2,3-dihydro-4-oxo-5-phenyl-4H-1,3-oxazin-3-yl)-2-methylpropanoate (7.56 g), as an oil, NMR (CDCl$_3$)δ 0.7–0.78(m,2H), 0.95–1.01(m,2H), 1.22(t,3H), 1.54(s,6H), 1.52–1.61(m,1H), 4.14(q,2H), 5.17(s,2H), 7.21–7.42(m,5H).

REFERENCE EXAMPLE 20

Jones reagent (65 ml), prepared from chromium trioxide (9.4 g), sulphuric acid (8.4 ml) and water, was added dropwise to a solution of methyl 3-cyclopropyl-3-hydroxy-2-phenylpropanoate (13.66 g) in acetone stirred at 0° C. After 1 hour at 0° C., and 2 hours at room temperature, the mixture was quenched (methanol) and evaporated. Water was added to the residue which was extracted (ether), dried (magnesium sulphate) and evaporated. The residue was purified by silica gel chromatography eluting with hexane-jethyl acetate (3:1) to give 3-cyclopropyl-3-oxo-2-phenylpropanoate (11.5 g) as an oil, NM $(CDCl_3)\delta$ 0.8–0.96 (m,2H), 1.02–1.17(m,2H), 1.88–1.99(m,1H), 3.76(s,3H), 4.87(s,1H), 7.27–7.43(m,5H).

REFERENCE EXAMPLE 21 n-Butyl lithium (46 ml of 1.69 M solution) was added to a mixture of diisopropylamine 7.8 g) in tetrahydrofuran stirred at −78 ° C. After 1 hour a solution of cyclopropyl-carboxaldehyde (4.91 g) in tetrahydrofuran was added at −78° C. and the mixture stirred for 0.5 hour. Ammonium chloride solution was then added, and the mixture extracted (ether), dried (magnesium sulphate) and evaporated. The residue was purified by silica gel chromatography eluting with hexane/ethyl acetate (2:1) to give methyl 3-cyclopropyl-3-hydroxy-2-phenylpropanoate (10.3 g) as an oil, NMR $(CDCl_3)\delta$ −0.18—−0.07 and 0.15–0.58(m,4H), 0.7–0.91(m,1H), 2.38, 2.7(bs,1H), 3.44–3.65(m,1H), 3.7(s, 3H), 3.74,3.78(d,1H), 7.25,7.44(m,5H).

According to a further feature of the present invention, there are provided compositions suitable for herbicidal use comprising one or more of the 1,3-oxazin-4-one derivative of formula (I) or an agriculturally acceptable salt thereof, in association with, and preferably homogeneously dispersed in, one or more compatible agriculturally-acceptable diluents or carriers and/or surface active agents [i.e. diluents or carriers and/or surface active agents of the type generally accepted in the art as being suitable for use in herbicidal compositions and which are compatible with compounds of formula (I)]. The term "homogeneously dispersed" is used to include compositions in which the compounds of formula (I) are dissolved in other components. The term "herbicidal compositions" is used in a broad sense to include not only compositions which are ready for use as herbicides but also concentrates which must be diluted before use. Preferably, the compositions contain from 0.05 to 90% by weight of one or more compounds of formula (I).

The herbicidal compositions may contain both a diluent or carrier and surface-active (e.g. wetting, dispersing, or emulsifying) agent. Surface-active agents which may be present in herbicidal compositions of the present invention may be of the ionic or non-ionic types, for example sulphoricinoleates, quaternary ammonium derivatives, products based on condensates of ethylene oxide with alkyl and polyaryl phenols, e.g. nonyl- or octyl-phenols, or carboxylic acid esters of anhydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphonosuccinates and alkali and alkaline earth metal salts of high molecular weight sulphonic acid derivatives such as sodium and calcium lignosulphonates and sodium and calcium alkylbenzene sulphonates.

Suitably, the herbicidal compositions according to the present invention may comprise up to 10% by weight, e.g. from 0.05% to 10% by weight, of surface-active agent but, if desired, herbicidal compositions according to the present invention may comprise higher proportions of surface-active agent, for example up to 15% by weight in liquid emulsifiable suspension concentrates and up to 25% by weight in liquid water soluble concentrates.

Examples of suitable solid diluents or carriers are aluminium silicate, microfine silicon dioxide, talc, chalk, calcined magnesia, kieselguhr, tricalcium phosphate, powdered cork, adsorbent carbon black and clays such as kaolin and bentonite. The solid compositions (which may take the form of dusts, granules or wettable powders) are preferably prepared by grinding the compounds of formula (I) with solid diluents or by impregnating the solid diluents or carriers with solutions of the compounds of formula (I) in volatile solvents, evaporating the solvents and, if necessary, grinding the products so as to obtain powders. Granular formulations may be prepared by absorbing the compounds of formula (I) (dissolved in suitable solvents, which may, if desired, be volatile) onto the solid diluents or carriers in granular form and, if desired, evaporating the solvents, or by granulating compositions in powder form obtained as described above. Solid herbicidal compositions, particularly wettable powders and granules, may contain wetting or dispersing agents (for example of the types described above), which may also, when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, glycols, glycol ethers, tetrahydrofuran alcohol, acetophenone, cyclohexanone, isophorone, N-alkyl pyrrolidones, toluene, xylene, mineral, animal and vegetable oils, esterified vegetable oils and light aromatic and naphthenic fractions of petroleum (and mixtures of these diluents). Surface-active agents, which may be present in the liquid compositions, may be ionic or non-ionic (for example of the types described above) and may, when liquid, also serve as diluents or carriers.

Powders, dispersible granules and liquid compositions in the form of concentrates may be diluted with water or other suitable diluents, for example mineral or vegetable oils, particularly in the case of liquid concentrates in which the diluent or carrier is an oil, to give compositions ready for use.

When desired, liquid compositions of the compound of formula (I) may be used in the form of self-emulsifying concentrates containing the active substances dissolved in the emulsifying agents or in solvents containing emulsifying agents compatible with the active substances, the simple addition of such concentrates to water producing compositions ready for use.

Liquid concentrates in which the diluent or carrier is an oil may be used without further dilution using the electrostatic spray technique.

Herbicidal compositions according to the present invention may also contain, if desired, conventional adjuvants such as adhesives, protective colloids, thickeners, penetrating agents, spreading agents, stabilisers, sequestering agents, anti-caking agents, colouring agents and corrosion inhibitors. These adjuvants may also serve as carriers or diluents.

Unless otherwise specified, the following percentages are by weight. Preferred herbicidal compositions according to the present invention are aqueous suspension concentrates which comprise from 10 to 70% of one or more compounds of formula (I), from 2 to 10% of surface-active agent, from 0.1 to 5% of thickener and from 15 to 87.9% of water;

wettable powders which comprise from 10 to 90% of one or more compounds of formula (I), from 2 to 10% of surface-active agent and from 8 to 88% of solid diluent or carrier;

water soluble or water dispersible powders which comprise from 10 to 90% of one or more compounds of formula (I), from 2 to 40% of sodium carbonate and from 0 to 88% of solid diluent;

liquid water soluble concentrates which comprise from 5 to 50%, e.g. 10 to 30%, of one or more compounds of formula (I), from 0 to 25% of surface-active agent and from 10 to 90%, e.g. 45 to 85%, of water miscible solvent, e.g. triethylene glycol, or a mixture of water-miscible solvent and water;

liquid emulsifiable suspension concentrates which comprise from 10 to 70% of one or more compounds of formula (I), from 5 to 15% of surface-active agent, from 0.1 to 5% of thickener and from 10 to 84.9% of organic solvent, e.g. mineral oil;

water dispersible granules which comprise from 1 to 90%, e.g. 25 to 75% of one or more compounds of formula (I), from 1 to 15%, e.g. 2 to 10%, of surface-active agent and from 5 to 95%, e.g. 20 to 60%, of solid diluent, e.g. clay, granulated with the addition of water to form a paste and then dried and emulsifiable concentrates which comprise 0.05 to 90%, and preferably from 1 to 60% of one or more compounds of formula (I), from 0.01 to 10%, and preferably from 1 to 10%, of surface-active agent and from 9.99 to 99.94%, and preferably from 39 to 98.99%, of organic solvent.

Herbicidal compositions according to the present invention may also comprise the compounds of formula (I) in association with, and preferably homogeneously dispersed in, one or more other pesticidally active compounds and, if desired, one or more compatible pesticidally acceptable diluents or carriers, surface-active agents and conventional adjuvants as hereinbefore described.

Examples of other pesticidally active compounds which may be included in, or used in conjunction with, the herbicidal compositions of the present invention include herbicides, for example to increase the range of weed species controlled for example alachlor [2-chloro-2,6'-diethyl-N-(methoxy-methyl)-acetanilide], atrazine [2-chloro-4-ethylamino-6-isopropylamino-1,3,5-triazine], bromoxynil [3,5-dibromo-4-hydroxybenzonitrile], chlortoluron [N'-(3-chloro-4-methylphenyl)-N,N-dimethylurea], cyanazine [2-chloro-4-(1-cyano-1-methylethylamino)-6-ethylamino-1,3,5-triazine], 2,4-D [2,4-dichlorophenoxy-acetic acid], dicamba [3,6-dichloro-2-methoxybenzoic acid], difenzoquat [1,2-dimethyl-3,5-diphenylpyrazolium salts], flampropmethyl [methyl N-2-(N-benzoyl-3-chloro-4-fluoroanilino)-propionate], fluometuron [N'-(3-trifluoromethylphenyl)-N,N-dimethylurea], isoproturon [N'-(4-isopropylphenyl)-N,N-dimethylurea], diclofop {(RS)-2-[4-2,4-dichlorophenoxy)phenoxy]propionic acid}, fenoxaprop and fenoxaprop-P {2-[4-(6-chloro-1,3-benzoxazol-2-yloxy)phenoxy]propionic acid}, diflufenican{N-(2,4-difluorophenyl)-2-[3-(trifluoromethyl) phenoxy]-3-pyridinecarboxamide}, tralkoxydin {2-[1-(ethoxyimino)propyl]-3-hydroxy-5-mesitylcyclohex-2-enone}, clodinafop {2-[4-(5-chloro-3-fluoro-2-pyridyloxy) phenoxy]propionic acid}, sulcotrione [2-(2-chloro-4-methylsulphonylbenzoyl)cyclohexane-1,3-dione], flurtamone {5-methylamino-2-phenyl-4-[3-(trifluoromethyl)phenyl]-3(2H)-furanone}, aclonifen (2-chloro-6-nitro-3-phenoxyaniline), and sulfonylureas (e.g. nicosulfuron); insecticides, e.g. synthetic pyrethroids, e.g. permethrin and cypermethrin, and fungicides, e.g. carbamates, e.g. methyl N-(1-butyl-carbamoyl-benzimidazol-2-yl)carbamate, and triazoles e.g. 1-(4-chlorophenoxy)-3,3-dimethyl-1-(1,2,4-triazol-1-yl)-butan-2-one.

Pesticidally active compounds and other biologically active materials which may be included in, or used in conjunction with, the herbicidal compositions of the present invention, for example those hereinbefore mentioned, and which are acids, may, if desired, be utilized in the form of conventional derivatives, for example alkali metal and amine salts and esters.

According to a further feature of the present invention there is provided an article of manufacture comprising at least one of the 1,3-oxazin-4-one derivative of formula (I) or, as is preferred, a herbicidal composition as hereinbefore described, and preferably a herbicidal concentrate which must be diluted before use, comprising at least one of the 1,3-oxazin-4-one derivative of formula (I) within a container for the aforesaid derivative or derivatives of formula (I), or a said herbicidal composition, and instructions physically associated with the aforesaid container setting out the manner in which the aforesaid derivative or derivatives of formula (I) or herbicidal composition contained therein is to be used to control the growth of weeds. The containers will normally be of the types conventionally used for the storage of chemical substances which are solid at normal ambient temperatures and herbicidal compositions particularly in the form of concentrates, for example cans and drums of metal, which may be internally lacquered, and plastics materials, bottles or glass and plastics materials and, when the contents of the container is a solid, for example granular, herbicidal compositions, boxes, for example of cardboard, plastics materials and metal, or sacks. The containers will normally be of sufficient capacity to contain amounts of the 1,3-oxazin-4-one derivative or herbicidal compositions sufficient to treat at least one acre of ground to control the growth of weeds therein but will not exceed a size which is convenient for conventional methods of handling. The instructions will be physically associated with the container, for example by being printed directly thereon or on a label or tag affixed thereto. The directions will normally indicate that the contents of the container, after dilution if necessary, are to be applied to control the growth of weeds at rates of application between 0.5 g and 5000 g of active material per hectare in the manner and for the purposes hereinbefore described.

The following Examples illustrate herbicidal compositions according to the present invention. The following trade marks appear in the description: Ethylan, Soprophor, Sopropo, Rhodorsil, Atagel, Synperonic, Solvesso, Arkopon, Tixosil.

Example C1:

A suspension concentrate is formed from:

| | |
|---|---|
| Oxazinone derivative (Compound 1) | 20% |
| Ethylan BCP (surfactant) | 0.5% |
| Soprophor FL | 0.5% |
| Sopropon T36 (Dispersant) | 0.2% |
| Rhodorsil 426R (Antifoaming agent) | 0.01% |

-continued

Example C1:

A suspension concentrate is formed from:

| | |
|---|---|
| Propylene glycol (antifreeze) | 5.0% |
| Atagel 50 (anti-settling agent) | 2.0% |
| Water | to 100% |

Similar suspension concentrates may be prepared by replacing Compound 1 with other oxazinone derivatives of formula (I).

Example C2

An emulsion concentrate is formed from the following:

| | |
|---|---|
| Oxazinone derivative (Compound 1) | 10% |
| Synperonic NPE1800 (surfactant) | 4.9% |
| Arylan CA (surfactant) | 5.0% |
| Cyclohexanone (solvent) | 9.8% |
| NMP (solvent) | 9.8% |
| Solvesso 150 (blending agent) | 5.0% |
| Water | to 100% |

Note: NMP means N-methylpyrollidine

Similar emulsion concentrates may be prepared by replacing Compound 1 with other oxazinone derivatives of formula (I).

Example C3

A wettable powder is formed from the following:

| | |
|---|---|
| Oxazinone derivative (Compound 1) | 20.0% |
| Arylan SX flake (surfactant) | 3.0% |
| Arkopon T (surfactant) | 5.0% |
| Sodium polycarboxylate (dispersant) | 1.0% |
| Tixosil 38 (flow aid) | 3.0% |
| China Clay | 68.0% |

Example C4

A wettable powder is formed from the following:

| | |
|---|---|
| Oxazinone derivative (Compound 1) | 20% |
| Clay | 70% |
| Calcium lignosulphate | 7% |
| Condensation product of alkylnaphthalene sulphonic acid-formalin | 3% |

The above mixture was mixed and ground with a jet mill to obtain 100 parts of wettable powder formulation.

Similar wettable powders may be prepared by replacing Compound 1 with other oxazinone derivatives of formula (I).

According to a feature of the present invention, there is provided a method for controlling the growth of weeds (i.e. undesired vegetation) at a locus which comprises applying to the locus a herbicidally effective amount of at least one 1,3-oxazin-4-one derivative of formula (I) or an agriculturally acceptable salt thereof. For this purpose, the 1,3-oxazin-4-one derivatives are normally used in the form of herbicidal compositions (i.e. in association with compatible diluents or carriers and/or surface active agents suitable for use in herbicidal compositions), for example as hereinafter described.

The compounds of formula (I) show herbicidal activity against dicotyledonous (i.e. broad-leafed) and monocotyledonous (e.g. grass) weeds by pre- and/or post-emergence application.

By the term "pre-emergence application" is meant application to the soil in which the weed seeds or seedlings are present before emergence of the weeds above the surface of the soil. By the term "post-emergence application" is meant application to the aerial or exposed portions of the weeds which have emerged above the surface of the soil. For example, the compounds of formula (I) may be used to control the growth of:

broad-leafed weeds, for example, Abutilon theophrasti, *Amaranthus retroflexus, Bidens pilosa, Chenopodium album, Galium aparine,* Ipomoea spp. e.g. *Ipomoea purpurea, Sesbania exaltata, Sinapis arvensis, Solanum nigrum* and *Xanthium strumarium*, and grass weeds, for example *Alopecurus myosuroides, Avena fatua, Digitaria sanguinalis, Echinochloa crus-galli, Eleusine indica* and Setaria spp, e.g. *Setaria faberii* or *Setaria viridis,* and sedges, for example, *Cyperus esculentus.*

The amounts of compounds of formula (1) applied vary with the nature of the weeds, the compositions used, the time of application, the climatic and edaphic conditions and (when used to control the growth of weeds in crop-growing areas) the nature of the crops. When applied to a crop-growing area, the rate of application should be sufficient to control the growth of weeds without causing substantial permanent damage to the crop. In general, taking these factors into account, application rates between palm and rubber plantations. For this purpose they may be applied in a directional or non-directional fashion (e.g. by directional or non-directional spraying) to the weeds or to the soil in which they are expected to appear, before or after planting of the trees or plantations at application rates between 50 g and 5000 g, and preferably between 50 g and 2000 g, most preferably between 100 g and 1000 g of active material per hectare.

The compounds of formula (I) may also be used to control the growth of weeds, especially those indicated above, at loci which are not crop-growing areas but in which the control of weeds is nevertheless desirable.

Examples of such non-crop-growing areas include airfields, industrial sites, railways, roadside verges, the verges of rivers, irrigation and other waterways, scrublands and fallow or uncultivated land, in particular where it is desired to control the growth of weeds in order to reduce fire risks. When used for such purposes in which a total herbicidal effect is frequently desired, the active compounds are normally applied at dosage rates higher than those used in crop-growing areas as hereinbefore described. The precise dosage will depend upon the nature of the vegetation treated and the effect sought.

Pre- or post-emergence application, and preferably pre-emergence application, in a directional or non-directional fashion (e.g. by directional or non-directional spraying) at application rates between 50 g and 5000 g, and preferably between 50 g and 2000 g, most preferably between 100 g and 1000 g of active 1 g and 1000 g of active material per hectare give good results. However, it is to be understood that higher or lower application rates may be used, depending upon the particular problem of weed control encountered.

The compounds of formula (I) may be used to control selectively the growth of weeds, for example to control the growth of those species hereinbefore mentioned, by pre- or post-emergence application in a directional or non-directional fashion, e.g. by directional or non-directional spraying, to a locus of weed infestation which is an area used, or to be used, for growing crops, for example cereals, e.g. wheat, barley, oats, maize and rice, soya beans, field and dwarf beans, peas, lucerne, cotton, peanuts, flax, onions, carrots, cabbage, oilseed rape, sunflower, sugar beet, and permanent or sown grassland before or after sowing of the crop or before or after emergence of the crop. For the selective control of weeds at a locus of weed infestation which is an area used, or to be used, for growing of crops, e.g. the crops hereinbefore mentioned, application rates between 10 g and 500 g, and preferably between 25 g and 250 g, of active material per hectare are particularly suitable.

The compounds of the invention are especially useful for controlling small seeded grass species, such as *Alopecurus myosuroides, Poa annua*, and *Apera spica-venti.*

The compounds of formula (I) may also be used to control the growth of weeds, especially those indicated above, by pre- or post-emergence application in established orchards and other tree-growing areas, for example forests, woods and parks, and plantations, e.g. sugar cane, oil material per hectare are particularly suitable for this purpose.

When used to control the growth of weeds by pre-emergence application, the compounds of formula (I) may be incorporated into the soil in which the weeds are expected to emerge. It will be appreciated that when the compounds of formula (I) are used to control the growth of weeds by post-emergence application, i.e. by application to the aerial or exposed portions of emerged weeds, the compounds of formula (I) will also normally come into contact with the soil and may also then exercise a pre-emergence control on later-germinating weeds in the soil.

Where especially prolonged weed control is required, the application of the compounds of formula (I) may be repeated if required.

METHOD OF USE OF HERBICIDAL COMPOUNDS

TEST METHOD A a) General

Appropriate quantities of the compounds used to treat the plants were dissolved in acetone to give solutions equivalent to application rates of up to 1000 g test compound per hectare (g/ha). These solutions were applied from a standard laboratory herbicide sprayer delivering the equivalent of 290 liters of spray fluid per hectare.

b) Weed control: Pre-emergence

The seeds were sown in 70 mm square, 75 mm deep plastic pots in non-sterile soil. The quantities of seed per pot were as follows:

| Weed species | | Approx number of seeds/pot |
|---|---|---|
| 1) Broad-leafed weeds | | |
| | *Abutilon theophrasti* | 10 |
| | *Amaranthus retroflexus* | 20 |
| | *Galium aparine* | 10 |
| | *Ipomoea purpurea* | 10 |
| | *Sinapis arvensis* | 15 |
| | *Xanthium strumarium* | 2. |
| 2) Grass weeds | | |
| | *Alopecurus myosuroides* | 15 |
| | *Avena fatua* | 10 |
| | *Echinochloa crus-galli* | 15 |
| | *Setaria viridis* | 20 |
| 3) Sedges | | |
| | *Cyperus esculentus* | 3. |
| Crop | | |
| 1) Broad-leafed | | |
| | Cotton | 3 |
| | Soya | 3. |
| 2) Grass | | |
| | Maize | 2 |
| | Rice | 6 |
| | Wheat | 6. |

The compounds of the invention were applied to the soil surface, containing the seeds, as described in (a). A single pot of each crop and each weed was allocated to each treatment, with unsprayed controls and controls sprayed with acetone alone.

After treatment the pots were placed on capillary matting kept in a glass house, and watered overhead. Visual assessment of crop damage was made 20–24 days after spraying. The results were expressed as the percentage reduction in growth or damage to the crop or weeds, in comparison with the plants in the control pots.

c) Weed control: Post-emergence

The weeds and crops were sown directly into John Innes potting compost in 75 mm deep, 70 mm square pots except for Amaranthus which was pricked out at the seedling stage and transferred to the pots one week before spraying. The plants were then grown in the greenhouse until ready for spraying with the compounds used to treat the plants. The number of plants per pot were as follows:

| Weed species | | Number of plants per pot | Growth stage |
|---|---|---|---|
| 1) Broad leafed weeds | | | |
| | *Abutilon theophrasti* | 3 | 1–2 leaves |
| | *Amaranthus retroflexus* | 4 | 1–2 leaves |
| | *Galium aparine* | 3 | 1st whorl |
| | *Ipomoea purpurea* | 3 | 1–2 leaves |
| | *Sinapis arvensis* | 4 | 2 leaves |
| | *Xanthium strumarium* | 1 | 2–3 leaves. |
| 2) Grass weeds | | | |
| | *Alopecurus myosuroides* | 8–12 | 1–2 leaves |
| | *Avena fatua* | 12–18 | 1–2 leaves |
| | *Echinochloa crus-galli* | 4 | 2–3 leaves |
| | *Setaria viridis* | 15–25 | 1–2 leaves. |
| 3) Sedges | | | |
| | *Cyperus esculentus* | 3 | 3 leaves. |

-continued

|  | Number of plants per pot | Growth stage |
|---|---|---|
| Crops | | |
| 1) Broad leafed Crops | | |
| Cotton | 2 | 1 leaf |
| Soya | 2 | 2 leaves. |
| 2) Grass Crops | | |
| Maize | 2 | 2–3 leaves |
| Rice | 4 | 2–3 leaves |
| Wheat | 5 | 2–3 leaves. |

The compounds used to treat the plants were applied to the plants as described in (a). A single pot of each crop and weed species was allocated to each treatment, with unsprayed controls and controls sprayed with acetone alone.

After treatment the pots were placed on capillary matting in a glass house, and watered overhead once after 24 hours and then by controlled sub-irrigation. Visual assessment of crop damage and weed control was made 20–24 days after spraying. The results were expressed as the percentage reduction in growth or damage to the crop or weeds, in comparison with the plants in the control pots.

TEST METHOD B (Paddy field foliar application)

Portions of paddy field soil and chemical fertiliser were put into plastic pots of 130 cm$^2$, and an appropriate amount of water was added to each pot, followed by sufficient mixing to make a sort of paddy field. Two-leaf stage paddy rice seedlings (c.v. Koshihikari) grown in advance in a greenhouse were transplanted to make one hill per pot with each hill consisting of two rice seedlings.

A number of seeds of Nobie (*Echinochloa oryzicola*), Kangi (*Monochoria vaginalis*), Azena (*Lindernia procumbens*), and Hotarui (*Scirpus juncoides*) were sown. Each pot was filled with water up to 3 cm deep. When the seeds of Nobie (*Echinochloa oryzicola*) had grown to the 1.5 leaf-stage in the greenhouse, wettable powder formula was prepared by the methods described in the Formulation example C4 diluted with the appropriate amount of water to make the content of active ingredients as 5 Kg or 1 Kg per ha, and applied with a pipette.

Visual assessments of crop damage and weed control was made 21 days after chemical treatment. The results were expressed as the percentage reduction in growth or damage to the crop or weeds, in comparison with the plants in the control pots.

TEST METHOD C (Paddy post-emergence application in greenhouse).

Paddy field soil was filled in 170 cm$^2$ plastic pots, a suitable amount of water and chemical fertilisers were added thereto and kneaded to convert it to a state of a paddy.

Paddy rice plants (variety; Koshihikari), that had been grown in advance in a greenhouse to a stage of two leaves, were transplanted to each pot (two seedlings per pot). Then in each pot there were sown predetermined amounts of seeds of *Echinochloa oryzicola, Monochoria vaginalis, Lindernia procumbens* and *Scirpus juncoides* respectively, and water was added to a depth of 3 cm.

After having grown the plants in a greenhouse until *Echinochloa oryzicola* reached a stage of 1.5 leaves, solutions were prepared in 100% acetone using compounds described in the Examples so that they contained active ingredients in an amount equivalent to 75,300 and 1200 g/ha. The solutions were applied by dropping with a pipette.

After 21 days from the application with the chemicals, herbicidal effects on each weed and phytotoxicity on paddy rice plants were visually assessed, and the results expressed as the percentage reduction in growth or damage to the crop or weeds in comparison with the plants in the control pots.

TEST METHOD D a) General

As in Test Method A above but the solutions were applied from an automated sprayer delivering the equivalent of 720 liters of spray fluid per hectare.

b) Weed control: Pre-emergence

The seeds were sown in 70 mm square, 75 mm deep plastic pots in non-sterile soil, 3 species per pot. The quantities of seed per pot were as follows:

|  |  | Approx number of seeds/species |
|---|---|---|
| Weed species | | |
| 1) Broad-leafed weeds | | |
| *Abutilon theophrasti* | | 7–8 |
| *Amaranthus retroflexus* | | 20 (pinch) |
| *Galium aparine* | | 4–5 |
| *Ipomoea purpurea* | | 5 |
| *Sinapis arvensis* | | 7–8 |
| *Matricaria inodora* | | 20 (pinch) |
| *Stellaria media* | | 20 (pinch) |
| 2) Grass weeds | | |
| *Alopecurus myosuroides* | | 15–20 |
| *Avena fatua* | | 10 |
| *Echinochloa crus-galli* | | 15 |
| *Setaria viridis* | | 15 |
| *Setaria faberii* | | 15 |
| *Apera spica-venti* | | 20 (pinch) |
| Crop | | |
| 1) Broad-leafed | | |
| Cotton | | 3 |
| Soya | | 2 |
| 2) Grass | | |
| Maize | | 2 |
| Rice | | 5 |
| Wheat | | 5 |

The compounds of the invention were applied to the soil surface, containing the seeds, as described in (a). Pots containing the species represented were allocated to each treatment, with unsprayed controls and controls sprayed with acetone alone.

After treatment the pots were placed on capillary matting kept in a glass house, and watered overhead. Visual assessment of crop damage was made 17 days after spraying. The results were expressed as the percentage reduction in growth or damage to the crop or weeds, in comparison with the plants in the control pots.

When applied pre- or post-emergence in Test Method A at 1000 g/ha or less, compounds 2–7, 15, 24, 25, 31, 33–37, 99–114, 116, 117, 119, 121–129 and 131–141 of the invention gave at least 80% reduction in growth of one or more of the weed species.

When applied at 1000 g/ha in Test Method B, compounds 8 and 141 of the invention gave at least 90% reduction in growth of one or more weed species.

When applied at 1200 g/ha or less in Test Method C, compounds 1–7, 13, 15, 24, 25, 31, 33–37, 99–104, 106–128, 131–133 and 137–140 of the invention gave at least 80% reduction in growth of one or more of the weed species.

When applied at 700 g/ha pre- or post-emergence in Test Method D, compound 9 of the invention gave at least 80% reduction in growth of one or more weed species.

At levels of applications toxic to the weeds these compounds were selective in at least one crop species.

It is claimed:

1. A 1,3-oxazin-4-one derivative of the formula (I):

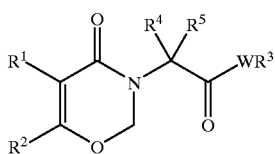

(I)

wherein:

$R^1$ represents phenyl optionally substituted by from one to five groups which may be the same or different selected from halogen, hydroxy, lower alkyl, haloalkyl, alkoxy, haloalkoxy, $-S(O)_nR^7$, $-CO_2R^7$, $-COR^7$, cyano, nitro, $-O(CH_2)_q-CO_2R^7$ and phenoxy;

$R^2$ represents:
a straight- or branched-chain alkyl having from one to ten carbon atoms which is substituted by one or more groups $R^8$ which may be the same or different;
a straight- or branched-chain optionally halogenated alkenyl or alkynyl group having up to ten carbon atoms;
or a group selected from cyano, $-CHO$, $-COR^7$, $-CO_2H$, $-CO_2R^7$, $-COSR^7$, $-CONR^9R^{10}$, $-CH=NOH$, $-CH=NOR^7$, $-CH=NOCOR^7$, $-CH=NNR^9R^{10}$, $-CH_2CN$, $-CH_2NO_2$ and oxiranyl;

$R^3$ represents phenyl optionally substituted by from one to five groups which may be the same or different selected from halogen, hydroxy, lower alkyl, haloalkyl, alkoxy, haloalkoxy, $-S(O)_nR^7$, $-CO_2R^7$, $-COR^7$, cyano, nitro, $-O(CH_2)_qCO_2R^7$ and phenoxy;
or $R^3$ represents a first five to seven membered heteroaromatic ring having from one to four ring heteroatoms which may be the same or different selected from nitrogen, oxygen and sulphur, said first ring being optionally fused to a phenyl ring or to a second five to seven membered heteroaromatic ring having from one to four heteroatoms which may be the same or different selected from nitrogen, oxygen and sulphur, to form a bicyclic ring system in which either ring is optionally substituted by from one to four groups which may be the same or different selected from halogen, hydroxy, lower alkyl, haloalkyl, alkoxy, haloalkoxy, $-S(O)_nR^7$, $-CO_2R^7$, $-COR^7$, cyano, nitro, $-O(CH_2)_qCO_2R^7$ and phenoxy, said first ring being linked to the nitrogen atom of the group $NR^6$ via one of the ring carbon atoms;

$R^4$ and $R^5$ independently represent lower alkyl;

W represents $-NR^6-$;

$R^6$ represents hydrogen, lower alkyl, haloalkyl, alkenyl, alkynyl, $-COR^7$ or $-CO_2R^7$;

$R^7$ represents lower alkyl or haloalkyl;

n represents zero, one or two;

q represents one or two;

$R^8$ represents a member of the group consisting of halogen, $-OH$, $-OR^7$, $-OCOR^7$, $-S(O)_nR^7$ and $-NR^9R^{10}$;

$R^9$ and $R^{10}$ independently represent hydrogen, lower alkyl or haloalkyl;

or an agriculturally acceptable salt thereof.

2. A compound according to claim 1 in which $R^1$ represents phenyl optionally substituted by one or more groups selected from halogen, lower alkyl and haloalkyl.

3. A compound according to claim 2 in which $R^1$ represents phenyl.

4. A compound according to claim 1, 2 or 3 in which $R^2$ represents a straight- or branched-chain alkyl having from one to four carbon atoms substituted by one to three groups $R^8$ which may be the same or different.

5. A compound according to claim 4 in which $R^2$ represents methyl substituted by one to three groups $R^8$ which may be the same or different.

6. A compound according to any one of claims 1 to 3 in which $R^8$ represents $-S(O)_nR^7$, (wherein $R^7$ is alkyl) or halogen.

7. A compound according to claim 6 in which $R^7$ is methyl.

8. A compound according to any one of claims 1 to 3 in which $R^2$ represents methyl substituted by fluorine, methoxy, ethoxy or $-S(O)_nCH_3$.

9. A compound according to claim 1 in which $R^6$ is hydrogen.

10. A compound according to claim 1 in which $R^3$ represents phenyl optionally substituted by one or two groups which be the same or different selected from halogen and haloalkyl.

11. A compound according to claim 1 in which $R^4$ and $R^5$ each represent methyl.

12. A compound according to claim 1 in which:
$R^1$ represents phenyl optionally substituted by one or more groups which may be the same or different selected from halogen, methoxy and optionally halogenated methyl;
$R^2$ represents methyl substituted by a fluorine atom, $-S(O)_nR^7$, $-OCH_3$ or $-OCH_2CH_3$;
$R^3$ represents a phenyl ring substituted by one to three groups which may be the same or different selected from halogen, optionally halogenated methyl and $NO_2$;
$R^4$ and $R^5$ represent methyl; and
W represents $-NH-$; and
$R^7$ represents optionally halogenated methyl.

13. A compound according to claim 1 in which:
$R^1$ represents unsubstituted phenyl;
$R^2$ represents a methyl group which is substituted by a group $R^8$;
a straight- or branched-chain alkyl containing from one to three carbon atoms which is substituted by one or more halogen atoms;
or a group selected from cyano, $-CHO$, $-CH=NOH$, $-CH=NOR^7$, $-CH=N-OCOCH_3$, $-CH=N-NHR^9$, $-COCH_3$, $-CH_2OH$ and $-CH(OH)CH_3$;
$R^3$ represents a phenyl ring substituted by one to three groups which may be the same or different selected from halogen or optionally halogenated methyl;
$R^4$ and $R^5$ represent methyl;
W represents $-NH-$;
$R^7$ represents methyl or ethyl; and
$R^8$ represents a member of the group consisting of $-OH$, $-OR^7$, $-OCOCH_3$, $-N(CH_3)_2$, $-NHCH_3$ and $-S(O)_nCH_3$.

14. A compound according to claim 1 which is:
N-(2,5-difluorophenyl)-2-(2,3-dihydro-6-methylsulphonylmethyl-4-oxo-5-phenyl-4H-1,3-oxazin-3-yl)-2-methylpropanamide N-(2,5-difluorophenyl)-2-(2,3-dihydro-6-methylthiomethyl-4-oxo-5-phenyl-4H-1,3-oxazin-3-yl)-2-methylpropanamide N-(3-trifluoromethylphenyl)-2-(2,3-dihydro-6-methylthiomethyl-4-oxo-5-phenyl-4H-1,3-oxazin-3-yl)-2-methylpropanamide N-(3-trifluoromethylphenyl)-2-(6-difluoromethyl-2,3-dihydro-4-oxo-5-phenyl-4H-1,3-oxazin-3-yl)-2-methylpropanamide N-(3,5-dichlorophenyl)-2-(6-bromomethyl-2,3-dihydro-4-oxo-5-phenyl-4H-1,3-oxazin-3-yl)-2-methylpropanamide N-(2,5-difluorophenyl)-2-(6-bromomethyl-2,3-dihydro-4-oxo-5-phenyl-4H-1,3-oxazin-3-yl)-2-methylpropanamide N-(3,5-dichlorophenyl)-2-(2,3-dihydro-6-methoxymethyl-4-oxo-5-phenyl-4H-1,3-oxazin-3-yl)-2-methylpropanamide N-(2,5-difluorophenyl)-2-(2,3-dihydro-6-methoxymethyl-4-oxo-5-phenyl-4H-1,3-oxazin-3-yl)-2-methylpropanamide N-(3-trifluoromethylphenyl)-2-(2,3-dihydro-6-methoxymethyl-4-oxo-5-phenyl-4H-1,3-oxazin-3-yl)-2-methylpropanamide N-(3,5-dichlorophenyl)-2-(6-fluoromethyl-2,3-dihydro-4-oxo-5-phenyl-4H-1,3-oxazin-3-yl)-2-methylpropanamide N-(2,5-difluorophenyl)-2-(6-fluoromethyl-2,3-dihydro-4-oxo-5-phenyl-4H-1,3-oxazin-3-yl)-2-methylpropanamide N-(2,5-difluorophenyl)-2-(6-chloromethyl-2,3-dihydro-4-oxo-5-phenyl-4H-1,3-oxazin-3-yl)-2-methylpropanamide N-(3,5-dichlorophenyl)-2-(6-chloromethyl-2,3-dihydro-4-oxo-5-phenyl-4H-1,3-oxazin-3-yl)-2-methylpropanamide N-(3-trifluorophenyl)-2-(6-chlcromethyl-2,3-dihydro-4-oxo-5-phenyl-4H-1,3-oxazin-3-yl)-2-methylpropanamide N-(5-chloro-2-methylphenyl)-2-(2,3-dihydro-6-methoxymethyl-4-oxo-5-phenyl-4H-1,3-oxazin-3-yl)-2-methylpropananide N-(3-chlorophenyl)-2-(2,3-dihydro-6-methoxymethyl-4-oxo-5-phenyl-4H-1,3-oxazin-3-yl)-2-methylpropanamide N-(2-fluoro-5-trifluoromethylphenyl)-2-(2,3-dihydro-6-methoxymethyl-4-oxo-5-phenyl-4H-1,3-oxazin-3-yl)-2-methylpropanamide N-(2,5-difluorophenyl)-2-(6-ethoxymethyl-2,3-dihydro-4-oxo-5-phenyl-4H-1,3-oxazin-3-yl)-2-methylpropanamide N-(3-trifluoromethylphenyl)-2-(6-ethoxymethyl-2,3-dihydro-4-oxo-5-phenyl-4H-1,3-oxazin-3-yl)-2-methylpropanamide N-(3,5-dichlorophenyl)-2-(6-ethoxymethyl-2,3-dihydro-4-oxo-5-phenyl-4H-1,3-oxazin-3-yl)-2-methylpropanamide N-(2-fluoro-5-trifluoromethylphenyl)-2-(6-fluoromethyl-2,3-dihydro-4-oxo-5-phenyl-4H-1,3-oxazin-3-yl)-2-methylpropanamide N-(3,4,5-trifluorophenyl)-2-(6-fluoromethyl-2,3-dihydro-4-oxo-5-phenyl-4H-1,3-oxazin-3-yl)-2-methylpropanamide N-(3,5-difluorophenyl)-2-(6-fluoromethyl-2,3-dihydro-4-oxo-5-phenyl-4H-1,3-oxazin-3-yl)-2-methylpropanamide N-(2-chloro-3,5-difluorophenyl)-2-(6-fluoromethyl-2,3-dihydro-4-oxo-5-phenyl-4H-1,3-oxazin-3-yl)-2-methylpropanamide N-(3-trifluoromethylphenyl)-2-(6-fluoromethyl-2,3-dihydro-4-oxo-5-phenyl-4H-1,3-oxazin-3-yl)-2-methylpropanamide N-(3-chlorophenyl)-2-(6-fluoromethyl-2,3-dihydro-4-oxo-5-phenyl-4H-1,3-oxazin-3-yl)-2-methylpropanamide N-(3,5-dichlorophenyl)-2-[6-(3-chloropropyl)-2,3-dihydro-4-oxo-5-phenyl-4H-1,3-oxazin-3-yl]-2-methylpropanamide N-(3-chlorophenyl-2-[6-(3-chloropropyl)-2,3-dihydro-4-oxo-5-phenyl-4H-1,3-oxazin-3-yl]-2-methylpropanamide N-(3-trifluoromethylphenyl)-2-[6-(3-chloropropyl)-2,3-dihydro-4-oxo-5-phenyl-4H-1,3-oxazin-3-yl]-2-methylpropanamide N-(2,5-difluorophenyl)-2-[6-(3-chloropropyl)-2,3-dihydro-4-oxo-5-phenyl-4H-1,3-oxazin-3-yl]-2-methylpropanamide N-(2,5-difluorophenyl)-2-(2,3-dihydro-6-methylsulphinylmethyl-4-oxo-5-phenyl-4H-1,3-oxazin-3-yl)-2-methylpropanamide N-(3-trifluoromethylphenyl)-2-(2,3-dihydro-6-methylsulphinylmethyl-4-oxo-5-phenyl-4H-1,3-oxazin-3-yl)-2-methyl-propanamide N-(3-chlorophenyl)-2-(2,3-dihydro-6-iodomethyl-4-oxo-5-phenyl-4H-1,3-oxazin-3-yl)-2-methylpropanamide N-(3-chlorophenyl)-2-(6-bromomethyl-2,3-dihydro-4-oxo-5-phenyl-4H-1,3-oxazin-3-yl)-2-methylpropanamide N-(3-trifluoromethylphenyl)-2-(6-bromomethyl-2,3-dihydro-4-oxo-5-phenyl-4H-1,3-oxazin-3-yl)-2-methylpropananide N-(3-chlorophenyl)-2-(6-dibromomethyl-2,3-dihydro-4-oxo-5-phenyl-4H-1,3-oxazin-3-yl)-2-methylpropananide N-(3,5-dichlorophenyl-2-(2,3-dihydro-6-methylthiomethyl-4-oxo-5-phenyl-4H-1,3-oxazin-3-yl)-2-methylpropanamide N-(3,5-dichlorophenyl)-2-(6-ethylthiomethyl-2,3-dihydro-4-oxo-5-phenyl-4H-1,3-oxazin-3-yl)-2-methylpropanamide N-(3-trifluoromethylphenyl)-2-(6-ethylthiomethyl-2,3-dihydro-4-oxo-5-phenyl-4H-1,3-oxazin-3-yl)-2-methylpropananide N-(3-trifluoromethylphenyl)-2-(2,3-dihydro-6-hydroxymethyl-4-oxo-5-phenyl-4H-1,3-oxazin-3-yl)-2-methylpropanamide N-(3,5-dichlorophenyl)-2-(2,3-dihydro-6-hydroxymethyl-4-oxo-5-phenyl-4H-1,3-oxazin-3-yl)-2-methylpropanamide N-(2,5-difluorophenyl)-2-(2,3-dihydro-6-hydroxymethyl-4-oxo-5-phenyl-4H-1,3-oxazin-3-yl)-2-methylpropanamide N-(3-trifluoromethylphenyl)-2-(6-acetoxymethyl-2,3-dihydro-4-oxo-5-phenyl-4H-1,3-oxazin-3-yl)-2-methylpropanamide N-(3,5-dichlorophenyl)-2-(6-acetoxymethyl-2,3-dihydro-4-oxo-5-phenyl-4H-1,3-oxazin-3-yl)-2-methylpropanamide N-(3-trifluoromethylphenyl)-2-(2,3-dihydro-6-methylaminomethyl-4-oxo-5-phenyl-4H-1,3-oxazin-3-yl)-2-methylpropanamide N-(3-trifluoromethylphenyl)-2-(2,3-dihydro-6-dimethylaminomethyl-4-oxo-5-phenyl-4H-1,3-oxazin-3-yl)-2-methylpropanamide N-(3,5-dichlorophenyl)-2-(2,3-dihydro-6-dimethylaminomethyl-4-oxo-5-phenyl-4H-1,3-oxazin-3-yl)-2-methylpropanamide N-(3,5-dichlorophenyl)-2-(2,3-dihydro-6-methylaminomethyl-4-oxo-5-phenyl-4H-1,3-oxazin-3-yl)-2-methylpropanamide N-(3,5-dichlorophenyl)-2-(2,3-dihydro-6-formyl-4-oxo-5-phenyl-4H-1,3-oxazin-3-yl)-2-methylpropanamide N-(3,5-dichlorophenyl)-2-(6-acetyl-2,3-dihydro-4-oxo-5-phenyl-4H-1,3-oxazin-3-yl)-2-methylpropanamide N-(2,5-difluorophenyl)-2-(6-acetoxymethyl-2,3-dihydro-4-oxo-5-phenyl-4H-1,3-oxazin-3-yl)-2-methylpropanamide N-(2-chloro-5-methylphenyl)-2-(2,3-dihydro-6-methoxymethyl-4-oxo-5-phenyl-4H-1,3-oxazin-3-yl)-2-methylpropanoate N-(3,5-dichlorophenyl)-2-(2,3-dihydro-6-hydroxyiminomethylene-4-oxo-5-phenyl-4H-1,3-oxazin-3-yl)-2-methylpropanamide N-(3,5-dichlorophenyl)-2-(6-ethoxyiminomethylene-2,3-dihydro-4-oxo-5-phenyl-4H-1,3-oxazin-3-yl)-2-methylpropanamide N-(3,5-dichlorophenyl)-2-(2,3-dihydro-6-methoxyiminomethylene-4-oxo-5-phenyl-4H-1,3-oxazin-3-yl)-2-methylpropanamide N-(2,5-difluorophenyl)-2-(2,3-dihydro-6-methoxyiminomethylene-4-oxo-5-phenyl-4H-1,3-oxazin-3-yl)-2-methylpropananide N-(3,5-dichlorophenyl)-2-(6-acetoxyiminomethylene-2,3-dihydro-4-oxo-5-phenyl-4H-1,3-oxazin-3-yl)-2-methylpropanamide N-(3,5-dichlorophenyl)-2-(6-aminoiminomethylene-2,3-dihydro-4-oxo-5-phenyl-4H-1,3-oxazin-3-yl)-2-methylpropanamide N-(3,5-dichlorophenyl)-2-(2,3-dihydro-6-methylaminoiminomethylene-4-oxo-5-phenyl-4H-1,3-oxazin-3-yl)-2-methylpropanamide N-(3,5-dichlorophenyl)-2-(6-cyano-2,3-dihydro-4-oxo-5-phenyl-4H-1,3-oxazin-3-yl)-2-methylpropanamide N-(3,5-dichlorophenyl)-2[2,3-dihydro-6-(1-hydroxyethyl)-4-oxo-5-phenyl-4H-1,3-oxazin-3-yl]-2-methylpropanamide or N-(2,5-difluorophenyl)-2-(2,3-dihydro-6-formyl-4-oxo-5-phenyl-4H-1,3-oxazin-3-yl)-2-methylpropanamide.

15. A herbicidal composition comprising an effective amount of a 1,3-oxazin-4-one derivative according to any one of claims 1 to 3 and 9–14 or an agriculturally acceptable salt thereof, in association with an agriculturally acceptable diluent or carrier and/or surface acting agent.

16. A method for the control of weeds at a locus which comprises applying to said locus an effective amount of a 1,3-oxazin-4-one derivative according to any one of claims 1 to 3 and 9–14 or an agriculturally acceptable salt thereof.

17. A method according to claim 16 wherein the locus is an area to be used, or to be used for the growing of crops and the 1,3-oxazin-4-one derivative is applied at an application rate of from 0.001 to 1.0 kg/ha.

18. A process for the preparation of a 1,3-oxazin-4-one derivative of formula (I) as defined in claim 1 which comprises:

(a) the reaction of a compound of formula (II):

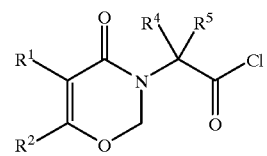

(II)

wherein $R^1$, $R^2$, $R^4$ and $R^5$ are as defined in claim 1, with an amine of formula (III):

$R^6NH—R^3$ (III)

wherein $R^3$ and $R^6$ are as defined in claim 1;

(b) where $R^2$ represents 3-chloropropyl, the chlorination of the corresponding compound of formula (IV):

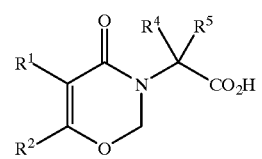

(IV)

wherein $R^1$, $R^4$ and $R^5$ are as defined in claim 1 and $R^2$ is replaced by cyclopropyl to give a compound of formula (II) wherein $R^2$ is 3-chloropropyl, followed by reaction with an amine of formula (III) as defined above;

(c) where W represents NH, the chlorination of a compound of formula (V):

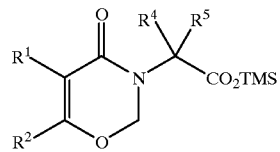

(V)

wherein $R^1$, $R^2$, $R^4$ and $R^5$ are as defined in claim 1 and TMS means trimethylsilyl to form a compound of formula (II) followed by reaction with an amine of formula (III);

(d) the reaction of a compound of formula (IV) above wherein $R^1$, $R^2$, $R^4$ and $R^5$ are as defined in claim 1, with an amine of formula (III) above wherein $R^3$ and $R^6$ are as defined in claim 1 in the presence of a coupling agent;

(e) where $R^6$ represents hydrogen, the reaction of a carboxylic acid of formula (IV) above wherein $R^1$, $R^2$, $R^4$ and $R^5$ are as defined in claim 1 with a phenyl carbamate of formula $PhO_2C—NHR^3$, wherein $R^3$ is as defined in claim 1, in the presence of a base;

(f) where $R^6$ represents a hydrogen, the reaction of a compound of formula (V) above wherein $R^1$, $R^2$, $R^4$ and $R^5$ are as defined in claim 1 and TMS means trimethylsilyl, with an amine of formula $—NH_2R^3$, wherein $R^3$ is as defined in claim 1;

(g) where $R^2$ represents —CHO, the oxidation of the corresponding compound of formula (I) wherein $R^2$ represents —CH$_2$OH;

(h) where $R^2$ represents —$COR^7$, the oxidation of the corresponding compound of formula (I) wherein $R^2$ represents —$CH(OH)R^7$;

(i) where $R^2$ represents an oxiranyl group, the reaction of the corresponding compound of formula (I) in wherein $R^2$ represents —CHO with a methylene transfer reagent;

(j) where $R^2$ represents alkenyl optionally substituted by halogen and wherein the double bond is located between the two carbon atoms closest to the 1,3-oxazin-4-one ring, the reaction of the corresponding compound of formula (I) wherein $R^2$ represents —CHO or —$COR^7$ with a phosphorane;

(k) where $R^2$ is —$CH(OH)R^{12}$ wherein $R^{12}$ represents a $C_1$–$C_9$ alkyl group the reaction of the corresponding compound of formula (I) in which $R^2$ represents —CHO with a Grignard reagent of formula $R^{12}Mg$—X wherein $R^{12}$ is as defined above and X represents a bromine or iodine;

(l) where $R^2$ represents —$CH_2OH$, the hydrolysis of the corresponding compound of formula (I) in which $R^2$ is —$CH_2OC(O)R^7$ wherein $R^7$ is as defined in claim 1;

(m) where $R^2$ represents difluoromethyl the fluorination of the corresponding compound of formula (I) in which $R^2$ represents —CHO;

(n) where $R^2$ represents —$CF_2R^7$, the fluorination of the corresponding compound of formula (I) in which $R^2$ represents —$COR^7$;

(o) where $R^2$ represents —$CH_2I$, the iodination of the corresponding compound of formula (I) wherein $R^2$ represents —$CH_2Br$ or —$CH_2Cl$;

(p) where $R^2$ represents —$C(Z)R^{12a}R^{12b}$, wherein Z represents bromine, chlorine or iodine and $R^{12a}$ and $R^{12b}$ represent hydrogen or an optionally halogenated alkyl group containing up to nine carbon atoms with the proviso that the total number of carbon atoms in the combined alkyl groups $R^{12a}$ and $R^{12b}$ does not exceed nine, the halogenation of the corresponding compound of formula (I) wherein $R^2$ represents —$CHR^{12a}R^{12b}$;

(q) where $R^2$ represents a $C_1$ to $C_{10}$ alkyl group substituted by a group —$SR^7$, the thiolation of the corresponding compound of formula (I) wherein the —$SR^7$ group is replaced by a leaving group;

(r) where $R^2$ represents a $C_1$ to $C_{10}$ alkyl group substituted by —$OC(O)R^7$ wherein $R^7$ is as defined in claim 1, the reaction of the corresponding compound of formula (I) in which the —$OC(O)R^7$ group is replaced by a leaving group, with a salt of formula $R^7$—$CO_2^-M_1^+$, wherein $M_1$ represents sodium or potassium;

(s) where $R^2$ represents —$CO_2R^7$, the esterification of the corresponding compound of formula (I) wherein $R^2$ represents —$CO_2H$, with an alcohol of formula $R^7OH$;

(t) where $R^2$ represents —$CO_2R^7$, the reaction of the corresponding compound of formula (I) wherein $R^2$ is replaced by —COCl with an alcohol of formula $R^7OH$;

(u) where $R^2$ represents a $C_1$ to $C_{10}$ alkyl group substituted by —$OR^7$ wherein $R^7$ is as defined in claim 1 the alkylation of the corresponding compound of formula (I) wherein —$OR^7$ is replaced by a hydroxy group;

(v) where $R^2$ represents a $C_1$–$C_{10}$ alkyl group substituted by —$OR^7$ wherein $R^7$ is as defined in claim 1, the reaction of the corresponding compound of formula (I) wherein —$OR^7$ is replaced by a hydroxy group with an alcohol of formula $R^7OH$ in the presence of a trialkylphosphine;

(w) where $R^2$ represents —CH=N—OH, the reaction of the corresponding compound of formula (I) wherein $R^2$ represents —CHO with hydroxylamine;

(x) where $R^2$ represents —CH=N—$OR^7$ wherein $R^7$ is as defined in claim 1, the reaction of the corresponding compound of formula (I) wherein $R^2$ represents —CHO with an O-alkylhydroxylamine of formula $R^7O$—$NH_2$;

(y) where $R^2$ represents —CH=N—$OCOR^7$ wherein $R^7$ is as defined in claim 1, the acylation of the corresponding compound of formula (I) wherein $R^2$ represents —CH=N—OH with an acid chloride of formula $R^7COCl$;

(z) where $R^2$ represents —CH=N—$NR^9R^{10}$, the reaction of the corresponding compound of formula (I) wherein $R^2$ represents —CHO with a hydrazine of formula $R^9R^{10}N$—$NH_2$;

(aa) where $R^2$ represents cyano, the dehydration of the corresponding compound of formula (I) wherein $R^2$ represents —CH=N—OH;

(ab) where $R^2$ represents —$COSR^7$ and $R^7$ is as defined in claim 1, the reaction of the corresponding compound of formula (I) wherein $R^2$ is replaced by —COCl with a thiol of formula $R^7SH$ wherein $R^7$ is as defined in claim 1;

(ac) where $R^2$ represents —$CH_2F$, the fluorination of the corresponding compound of formula (I) wherein $R^2$ represents —$CH_2OH$;

(ad) where $R^2$ represents —$CHFR^7$, the fluorination of the corresponding compound of formula (I) wherein $R^2$ represents —$CH(OR)R^7$;

(ae) where $R^2$ represents —$CONR^9R^{10}$ wherein $R^9$ and $R^{10}$ are as defined in claim 1, the reaction of the corresponding compound of formula (I) wherein $R^2$ is replaced by —COCl, with an amine of formula $R^9R^{10}NH$ wherein $R^9$ and $R^{10}$ are as defined in claim 1;

(af) where $R^2$ represents —$CO_2H$, the oxidation of the corresponding compound of formula (I) wherein $R^2$ represents —CHO;

(ag) where $R^2$ represents a $C_1$–$C_{10}$ alkyl group substituted by a group —$NR^9R^{10}$ the amination of the corresponding compound of formula (I) wherein the —$NR^9R^{10}$ group is replaced by a leaving group, preferably chloro or bromo, with an amine of formula $R^9R^{10}NH$;

(ah) where $R^6$ represents lower alkyl, alkenyl, alkenyl, —$COR^7$ or —$CO_2R^7$, the reaction of the corresponding compound of formula (I) wherein $R^6$ represents hydrogen with a compound of formula $R^{61}$—$X^1$ wherein $R^{61}$ represents lower alkyl, alkenyl, alkynyl, —$COR^7$ or —$CO_2R^7$ and $X^1$ represents a leaving group;

(ai) where n is one or two, the oxidation of the corresponding compound of formula (I) wherein n is zero or one;

optionally followed by conversion of the compound of formula (I) thus obtained into an agriculturally acceptable salt thereof.

19. A compound of formula (II), (IV), (V), (VI) and (VII):
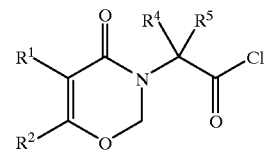 (II)
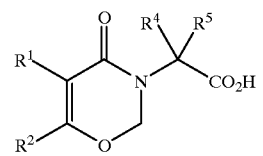 (IV)
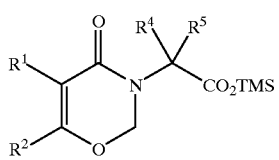 (V)
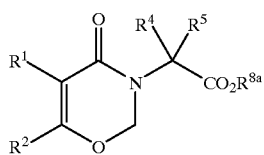 (VI)
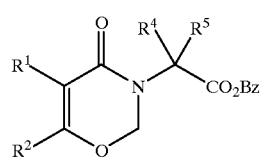 (VII)
wherein $R^1$, $R^2$, $R^4$ and $R^5$ are as defined in claim 1, $R^{8a}$ represents an alkyl group, TMS means trimethylsilyl and Bz represents benzyl.
* * * * *